(12) United States Patent
Sung et al.

(10) Patent No.: US 12,324,870 B2
(45) Date of Patent: *Jun. 10, 2025

(54) NASOLACRIMAL DUCT INSERTION MEMBER COMPRISING SHAPE MEMORY POLYMER

(71) Applicant: TMD LAB CO., LTD., Seoul (KR)

(72) Inventors: Hak-Joon Sung, Seoul (KR); Jin Sook Yoon, Seoul (KR); Jung Bok Lee, Seoul (KR); Jae Sang Ko, Seoul (KR); Woo Beom Shin, Seoul (KR)

(73) Assignee: TMD LAB CO., LTD, Seoul (KR)

( * ) Notice: Subject to any disclaimer, the term of this patent is extended or adjusted under 35 U.S.C. 154(b) by 1033 days.

This patent is subject to a terminal disclaimer.

(21) Appl. No.: 17/281,666

(22) PCT Filed: Oct. 1, 2019

(86) PCT No.: PCT/KR2019/012824
§ 371 (c)(1),
(2) Date: Mar. 31, 2021

(87) PCT Pub. No.: WO2020/071732
PCT Pub. Date: Apr. 9, 2020

(65) Prior Publication Data
US 2021/0369920 A1 Dec. 2, 2021

(30) Foreign Application Priority Data
Oct. 2, 2018 (KR) .................. 10-2018-0117796

(51) Int. Cl.
*A61L 29/14* (2006.01)
*A61L 29/04* (2006.01)
(Continued)

(52) U.S. Cl.
CPC ............. *A61L 29/041* (2013.01); *A61L 29/14* (2013.01); *C08G 63/08* (2013.01); *A61L 2400/16* (2013.01); *C08G 2280/00* (2013.01)

(58) Field of Classification Search
None
See application file for complete search history.

(56) References Cited

U.S. PATENT DOCUMENTS 11,628,235 B2 * 4/2023 Sung ................... A61L 27/26
528/356
2003/0215483 A1 11/2003 Kim et al.
(Continued)

FOREIGN PATENT DOCUMENTS

EP 3608346 A1 2/2020
JP 2018-522992 A 8/2018
(Continued)

OTHER PUBLICATIONS

International Search Report from corresponding PCT Application No. PCT/KR2018/012824, dated Jan. 29, 2020.
(Continued)

*Primary Examiner* — Michael J Feely
(74) *Attorney, Agent, or Firm* — Harness, Dickey & Pierce, P.L.C.

(57) ABSTRACT

The present invention relates to a nasolacrimal duct insertion member comprising a shape memory polymer for treatment of nasolacrimal duct obstruction/stenosis, wherein the shape memory polymer comprises a crosslinkable functional group, such that the nasolacrimal duct insertion member has a melting point suitable for implantation into a living body.

5 Claims, 19 Drawing Sheets

(51) Int. Cl.
  *C08G 63/08*   (2006.01)
  *C08L 67/04*   (2006.01)
  *C08L 67/06*   (2006.01)
  *C08L 67/07*   (2006.01)

(56) References Cited

U.S. PATENT DOCUMENTS

| | | |
|---|---|---|
| 2017/0049619 A1 | 2/2017 | Kahook |
| 2018/0126046 A1 | 5/2018 | Sung et al. |
| 2022/0000481 A1 | 1/2022 | Sung et al. |

FOREIGN PATENT DOCUMENTS

| | | | |
|---|---|---|---|
| KR | 2002/0054061 A | 7/2002 | |
| KR | 10-1606112 B1 | 3/2016 | |
| KR | 10-1906472 B1 | 10/2018 | |
| KR | 2019/0074117 A | 6/2019 | |
| KR | 2020/0038198 A | 4/2020 | |
| WO | WO-2010107826 A2 * | 9/2010 | ......... A61F 9/00772 |
| WO | WO-2018186575 A1 | 10/2018 | |

OTHER PUBLICATIONS

Shen, H. et al.; "Cross-linking and damping properties of poly(caprolactone-co-glycidyl methacrylate)", Polymer Journal, 2014, vol. 46, pp. 598-608.

Zhao, S-P, et al.; Synthesis and Properties of Photopolymerizaed pH-Sensitive Hydrogels of Methacrylic Acid and Biodegradable PEG-b-PCL Macromer:, Iranian Polymer Journal, 2011, vol. 20, No. 4, pp. 329-340.

Bicak, N., et al; "Synthesis of new polyesters with methacrylate pendant groups", Polymer Bulletin, 2006, vol. 56, No. 1, pp. 87-93.

Shin, Y. C. et al.; "Development of a Shape-Memory Tube to Prevent Vascular Stenosis", Adv. Mater., Aug. 27, 2019, vol. 31, No. 41, inner pp. 1-8.

Extended European Search Report from corresponding European Patent Application No. 19869808.6, dated Jun. 2, 2022.

Office Action from corresponding Japanese Patent Application No. 2021-544080, dated Apr. 26, 2022.

Notice of Allowance from corresponding Korean Patent Application No. 10-2018-0117796, dated Mar. 30, 2023.

* cited by examiner (a) (b)

NASOLACRIMAL DUCT INSERTION MEMBER COMPRISING SHAPE MEMORY POLYMER

CROSS-REFERENCE TO RELATED APPLICATIONS

This application is a national phase application of PCT Application No. PCT/KR2019/012824, filed on Oct. 1, 2019, which claims benefit of Korean Patent Application No. 10-2018-0117796, filed Oct. 2, 2018. The entire disclosure of the applications identified in this paragraph are incorporated herein by references.

TECHNICAL FIELD

The present invention relates to a nasolacrimal duct insertion member comprising a shape memory polymer. More specifically, the present invention relates to a nasolacrimal duct insertion member comprising a shape memory polymer for treatment of nasolacrimal duct obstruction/stenosis.

BACKGROUND ART

Human tears are secreted by the lacrimal glands situated along the inner surface of the upper eyelid and flow into an opening called lacrimal punctum (1, 1'). From the lacrimal punctum, tears enter the lacrimal sac (2), then on to the nasolacrimal duct (3), and finally into the nasal cavity (nose) before being discharged (FIG. 1(*a*)).

When narrowed or obstructed, the nasolacrimal duct (3), which is a canal carrying tears from the eye to the nose, has a poor tear discharge function. This leads to a disorder called epiphora wherein tears will excessively overflow, rather than drain through the nasolacrimal system. The obstruction may be congenital or acquired. Particularly, many cases of watery eyes in infants are attributed to congenital obstruction of nasolacrimal duct (3). Congenital obstruction of nasolacrimal duct (3) occurs when the lacrimal duct has failed to open at the time of birth, most often due to an imperforate membrane at the end of the nose. For adults, nasolacrimal duct obstruction is, in most part, acquired by factors including chronic inflammation, senescence, etc. Acquired nasolacrimal duct obstruction includes functional obstruction caused by lacrimal drainage dysfunction, without anatomical lacrimal duct obstruction, which leads to epiphora (FIG. 1*b*).

Recently, environmental changes incite production of excessive tears so that persons frequently suffer watery eyes. In an outdoor environment, xerophthalmia patients may secrete many tears due to stimuli such as wind blowing. In addition, persons suffering from allergies such as conjunctivitis, or corneal diseases, palpebritis, entropion of the eyelid, and the like may have watery eyes because intensive irritations affect the eyes.

In order to treat such symptoms, the obstructed or narrowed nasolacrimal duct is widened by inserting a silicone tube into the tear path and then removing the same after a certain period of time. Alternatively, when the nasolacrimal duct is completely blocked, dacryocystoplasty may be conducted, in which a new lacrimal duct is formed by dacryocrystorhinostomy and a silicone tube is inserted to the same and then maintained for a predetermined period of time before removal.

In general, a nasolacrimal duct insertion device that is used in dacryocystoplasty has a structure in which rod-shaped metallic probes are connected to opposite ends of a flexible tube. However, because nasolacrimal duct insertion devices according conventional techniques lack a passage which allows tears to pass therethrough, tears cannot be properly discharged, with the tube inserted into the human body.

After dacryocystoplasty is performed, the tube inserted should be maintained for at least three months or for up to six months. In this condition, produced tears can be discharged only a narrow passage between the tube and the lacrimal duct because the tube occupies most of the tear discharge passage. Hence, tears are not smoothly discharged, but are apt to stagnate, with the consequent high risk of infection.

In the meanwhile, active research has recently been conducted into biocompatible synthetic polymers for application to blood vessels or organs in the human body.

Synthetic polymers developed for application to human blood vessels or organs can be exemplified by poly(lactic acid) (PLA), poly(glycolic acid) (PGA), poly(lactic-co-glycolic acid) (PLGA), poly(ε-caprolactone) (PCL), etc.

Of them, poly(ε-caprolactone) (PCL) is a biocompatible and biodegradable polymer with capability of photocrosslinking and chemical modifications into shape memory polymers and has been approved for biomedical applications by the FDA.

However, the polymer has a melting point (Tm) of 45 to 65° C. which is too high to apply the polymer to physiological (37° C.) application devices, etc. Thus, such a problem limits the clinical applicability of the shape memory polymers such as poly(ε-caprolactone) (PCL). In addition, the use of other memory polymers for clinical purposes is also limited because it requires a methacrylate functionalization step or a monomer synthesis step.

Therefore, there is a need for the development of a shape memory polymer that is relatively non-invasive, does not cause a pain upon application to the human body, can be produced at low cost, and is available as a medical device member having a melting point suitable for use, particularly, in an artificial nasolacrimal duct, etc.

SUMMARY

Technical Problem

The present invention has been made to solve the above problems and is intended to provide a nasolacrimal duct insertion member comprising a shape memory polymer with a melting point suitable for bio-implantation.

Furthermore, the present invention provides a nasolacrimal duct insertion member easy to insert into the human body.

In addition, the present invention provides a method for production of a nasolacrimal duct insertion member comprising a shape memory polymer.

Moreover, the present invention provides a use of a shape memory polymer in a nasolacrimal duct insertion member.

Technical Solution

In order to achieve the purposes, an aspect of the present invention provides a nasolacrimal duct insertion member comprising a shape memory polymer represented by the following Chemical Formula 1:

[Chemical Formula 1]

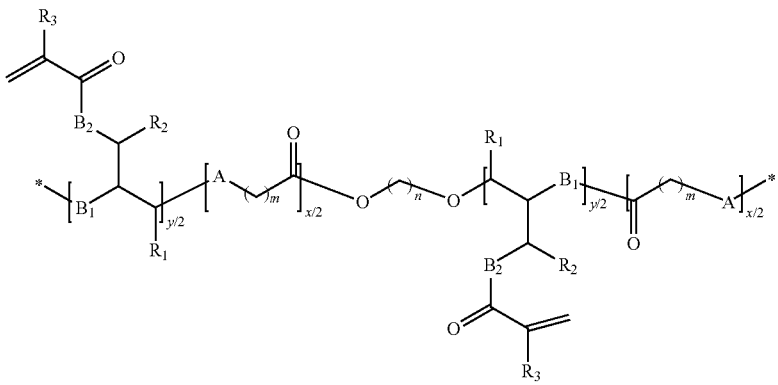

wherein,
$R_1$, $R_2$, and $R_3$ are each independently hydrogen (H) or an alkyl of 1 to 6 carbon atoms,
m and n are each an integer of 1 to 20,
A, $B_1$, and $B_2$ are each independently oxygen (O) or sulfur (S),
x and y represent mole % for respective repeat units, and x+y is 100, and x is 80 to 95.

Advantageous Effects

The nasolacrimal duct insertion member according to an embodiment of the present invention comprises a shape memory polymer bearing a crosslinkable functional group and thus has a melting point suitable for bio-implantation.

Based on a shape memory polymer, a nasolacrimal duct insertion member according to an embodiment of the present invention is particularly easy to insert into the nasolacrimal duct and can be applied to a narrowed or obstructed nasolacrimal duct and expand to smoothly discharge tears therethrough.

DETAILED DESCRIPTION

Figure 1:
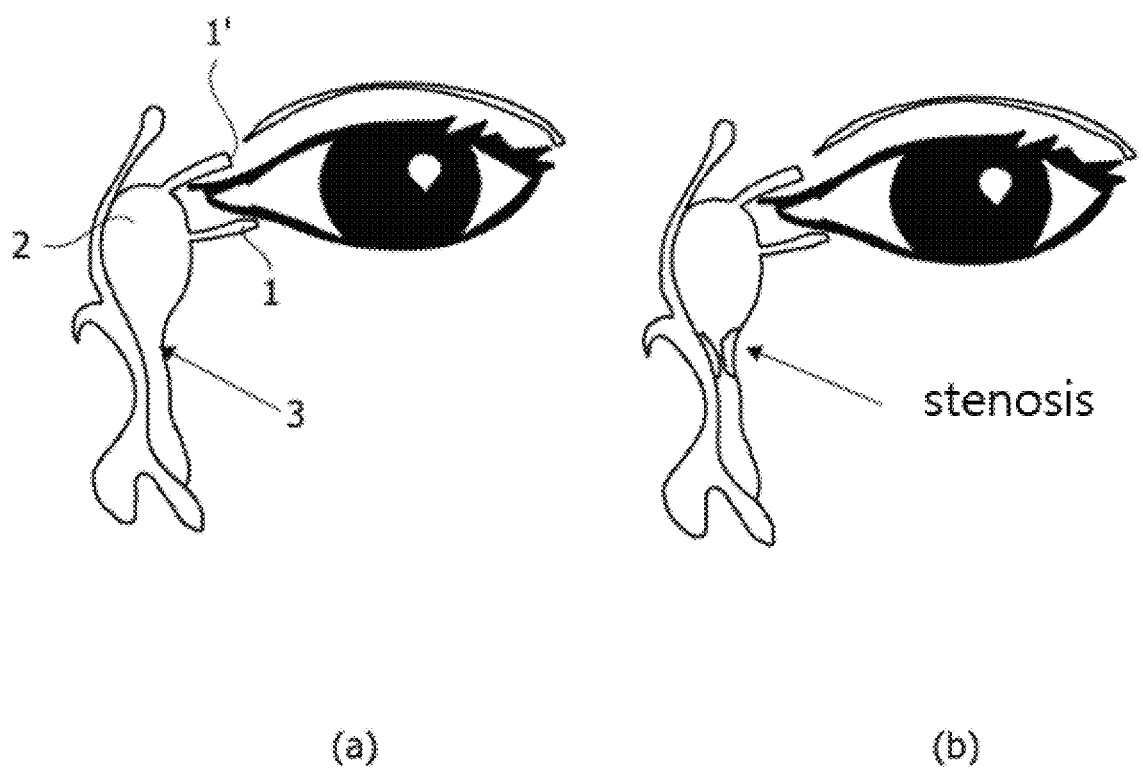
FIG. 1 is a view illustrating the nasolacrimal duct ((a) normal nasolacrimal duct and (b) narrowed nasolacrimal duct).

The present invention may have various modifications and various examples, and thus specific examples are illustrated in the drawings and described in detail in the detailed description.

However, it should be understood that the present invention is not limited to specific embodiments, and includes all modifications, equivalents or alternatives within the idea and technical scope of the present invention.

The terms "comprise", "have" or "consist of" used herein designate the presence of characteristics, numbers, steps, actions, components or members described in the specification or a combination thereof, and it should be understood that the possibility of the presence or addition of one or more other characteristics, numbers, steps, actions, components, members or a combination thereof is not excluded in advance.

In addition, the accompanying drawings in the present invention should be understood as being enlarged or reduced for convenience of description.

Hereinafter, embodiments will be described in detail with reference to the accompanying drawings. However, the same reference numbers will be assigned to the same or corresponding elements regardless of the figure number, and the overlapping descriptions thereof will be omitted.

As used herein, the term "nasolacrimal duct" refers to a membranous canal that begins in the eye socket between the maxillary and lacrimal bones and passes downwards and backwards, extending from the lower part of the lacrimal sac to the inferior meatus of the nose (this is why nose runs upon crying). The nasolacrimal duct is lined by stratified columnar epithelium, with the spongy venous plexus developed in the lamina propria thereof. When narrowed or obstructed, the nasolacrimal duct, which is a canal carrying tears from the eye to the nose, have a poor tear discharge function. This leads to a disorder called epiphora wherein tears will excessively overflow, rather than drain through the nasolacrimal system. The obstruction may be congenital or acquired. Particularly, many cases of watery eyes in infants are attributed to congenital obstruction of nasolacrimal duct. Congenital obstruction of nasolacrimal duct occurs when the lacrimal duct has failed to open at the time of birth, most often due to an imperforate membrane at the end of the nose. For adults, nasolacrimal duct obstruction is, in most part, acquired by factors including chronic inflammation, senescence, etc. Acquired nasolacrimal duct obstruction includes functional obstruction caused by lacrimal drainage dysfunction, without anatomical lacrimal duct obstruction, which leads to epiphora. Recently, environmental changes incite production of excessive tears so that persons frequently suffer watery eyes. In an outdoor environment, xerophthalmia patients may secrete many tears due to stimuli such as wind blowing. In addition, persons suffering from allergies such as conjunctivitis, or corneal diseases, palpebritis, entropion of the eyelid, and the like may have watery eyes because intensive irritations affect the eyes.

Most epiphora cases are attributed to nasolacrimal duct obstruction without anatomical abnormality and treated in a non-surgical manner, for example, by using a drug or inserting a guider (tube) to open the nasolacrimal duct.

Accordingly, the present invention provides a nasolacrimal duct insertion member for treatment of nasolacrimal duct obstruction/stenosis.

As used herein, the term "nasolacrimal duct insertion member" refers to a member to be inserted into an obstructed or narrowed nasolacrimal duct to make the same open, and may be an artificial nasolacrimal duct.

A nasolacrimal duct insertion member according to an embodiment of the present invention may comprise a shape memory polymer.

The term "shape memory polymer" (SMP), as used herein, refers to a polymer that has the ability to return to its original state by a suitable stimulus. In detail, a shape memory polymer means a polymer that undergoes the three steps of (1) being endowed with a permanent shape (initial shape) by processing, (2) being transformed into a temporary shape at a low temperature, and (3) returning to the original permanent shape in response to an external stimulus (temperature).

In the present invention, the stimulus may be "temperature". In detail, a shape memory polymer can return to the permanent shape thereof when heated to the transition temperature (glass transition temperature or melting point) thereof or higher. In this regard, the term "melting point" used herein may not refer to a temperature at which the polymer melts, but to a temperature at which the polymer returns to the original shape (initial shape) thereof.

The melting point of the shape memory polymer according to an embodiment of the present invention may be 30 to 48° C. on average, and may be lowered when the polymer is crosslinked. In detail, the shape memory polymer may have a melting point of 28 to 42° C. on average after it is crosslinked. That is, the nasolacrimal duct insertion member including the above-described shape memory polymer according to the present invention can return to its original shape (initial shape) at an average temperature of 28 to 42° C. The deformation is made at a temperature of 28 to 42° C. or higher, but the temperature should not exceed 50° C. that is a protein denaturation temperature. For example, the temperature at which the shape memory polymer is deformed may be in the range of 28 to 42° C., or higher than the range and less than 50° C. Accordingly, the nasolacrimal duct insertion member according to the present invention may be suitable for bio-implantation. Here, the crosslinking may be photocrosslinking or thermal crosslinking. By way of example, induction of a photocrosslinking reaction in the synthetic shape memory polymer can impart a shape to the nasolacrimal duct insertion member and lower the melting point of the shape memory polymer to 28 to 42° C.

The term "strain rate", as used in the context of a shape memory polymer, refers to a rate of shape change when a polymer is restored from a temporary shape to an initial shape and maintains a permanent shape, accounting for a rate of change from a temporary shape to a permanent shape. The term "deformation recovery rate" means a recovery ratio of the initial shape before deformation by a physical force from a temporary shape, describing a ratio of the permanent shape to the initial shape. In the present invention, the strain rate may vary depending on the ratio or conditions (temperature, UV, etc.) of the monomers included in the shape memory polymer, and may be specifically 5 to 350%. In addition, the deformation recovery rate may be 90% or more.

In addition, the nasolacrimal duct insertion member according to an embodiment of the present invention may comprise a biodegradable shape memory polymer. As used herein, the term "biodegradable" refers to pertaining to degradation by an enzyme secreted from a microorganism present in nature. When is applied to the biological body, the term means a property of being degraded in the body without almost no inflammation therein. Thus, the term "biodegradable shape memory polymer" refers to a polymer that is degraded and absorbed in the human body over time and can change in shape according to temperature changes. That is, it means a polymer having biodegradability among shape memory polymers that can change in shape with temperature changes.

Below, a detailed description will be given of the present invention.

The present invention provides a nasolacrimal duct insertion member comprising a shape memory polymer having a melting point suitable for bio-implantation.

In particular, the nasolacrimal duct insertion member of the present invention includes a shape-memory polymer and can be inserted in a thin temporary shape having a small diameter into the nasolacrimal duct. After insertion, the nasolacrimal duct insertion member can be restored to an initial shape from the temporary shape with the increase of the nasal tube insertion member in diameter. Accordingly, the nasolacrimal duct insertion member can widen an obstructed or narrowed nasolacrimal duct, thereby allowing tears to be easily discharged.

Made of a biodegradable shape memory polymer, the nasolacrimal duct insertion member can omit a post-operation process of removing the inserted nasolacrimal duct insertion member.

In an embodiment thereof, the present invention provides a nasolacrimal duct insertion member comprising a shape memory polymer represented by Chemical Formula 1:

[Chemical Formula 1]

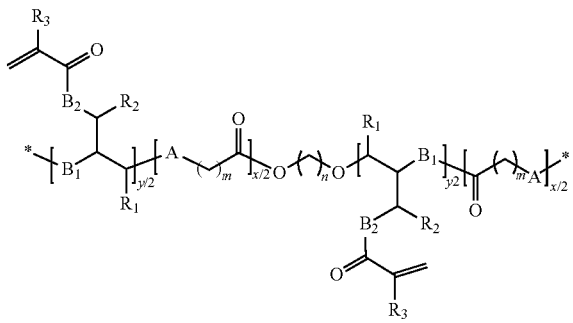

wherein,
$R_1$, $R_2$, and $R_3$ are each independently hydrogen (H) or an alkyl of 1 to 6 carbon atoms,
m and n are each an integer of 1 to 20,
A, $B_1$, and $B_2$ are each independently oxygen (O) or sulfur (S),
x and y represent mole % for respective repeat units, and x+y is 100, and x is 80 to 95.

In detail, in Chemical Formula 1,
$R_1$, $R_2$, and $R_3$ are each independently hydrogen (H) or a methyl group ($CH_3$—),
m and n are each an integer of 3 to 22,
A, $B_1$, and $B_2$ are each oxygen (O),
x and y represent mole % for respective repeat units, and x+y is 100, and x is 88 to 94.

In greater detail, in Chemical Formula 1,
$R_1$, $R_2$, and $R_3$ are each hydrogen (H),
m and n are each an integer of 5 to 6,
A, $B_1$, and $B_2$ are each oxygen (O),
x and y represent mole % for respective repeat units, and x+y is 100, and x is 88 to 94.

Chemical Formula 1 can be specified by the following Chemical Formula 2:

[Chemical Formula 2]

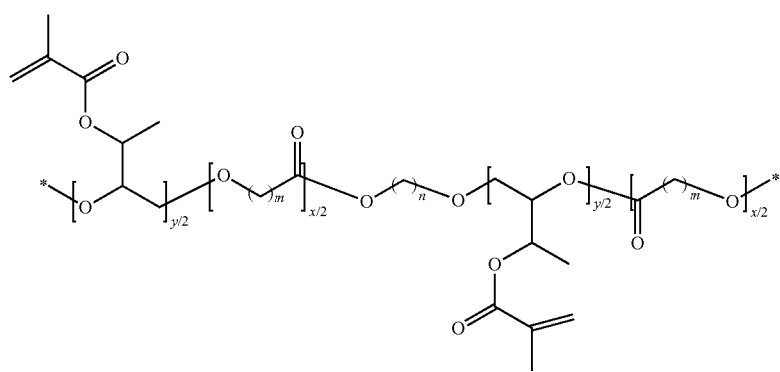

wherein, m and n are each independently an integer of 1 to 20, x and y represent mole % for respective repeat units, and x+y is 100, and x is 80 to 95.

The shape memory polymer according to the present invention may have a copolymer structure in which an ε-caprolactone monomer and a glycidyl group-bearing acryl monomer are polymerized. For example, the shape memory polymer may have a structure of copolymer [PCL-co-PGMA)] in which ε-caprolactone monomer (CL; caprolactone) and glycidyl methacrylate (GMA) are polymerized.

In the shape memory polymer according to the present invention, the ε-caprolactone monomers and the acryl monomers are not particularly limited by arrangement orders and may be arranged in alternating, random, or block patterns.

Moreover, the copolymer including the unit of Chemical Formula 1 or 2 may be coupled at the terminal thereof to a hydroxyl group, etc. Such a hydroxyl-terminated copolymer can be prepared by polymerization in the presence of an initiator having a hydroxyl group at the terminus thereof.

Moreover, the glycidyl group included in the acryl monomer may be a crosslinkable functional group, whether photo- or thermo-crosslinkable.

The melting point of the shape memory polymer according to an embodiment of the present invention can be adjusted according to the amounts of the components ε-caprolactone monomers and glycidyl-bearing acryl monomers therein.

More specifically, in Chemical Formula 1 or 2, x and y are mole % for respective repeat units, and x+y is 100, and x is 80 to 95 or from 88 to 94.

Here, the term "mole %" refers to a percentage for the repeat unit of each of x and y and specifically may mean a molar ratio. For example, it may mean mole ratios of PCL and PGMA in PCL-co-PGMA.

For reference, when x is less than 80 in Chemical Formula 1, the shape memory polymer may have a melting point less than 28° C. after crosslinking and thus may be difficult to apply to the human body due to the shape change at room temperature. When X exceeds 95, the melting point of the shape memory polymer is higher than 42° C. after crosslinking, which results in increasing the phase transition temperature of the shape memory polymer for shape recovery and thus makes it difficult to utilize the polymer on the basis of the human body temperature (37° C.).

Accordingly, the shape memory polymer may range in melting point from 30 to 48° C. and is given a lower melting point when being crosslinked.

More specifically, the shape memory polymer may have a melting point of 28 to 42° C. on average after crosslinking.

For reference, as described above, the crosslinked shape memory polymer with a melting point less than 28° C. has a limited application as physiological instruments because the material undergoes a shape change at room temperature. Given a melting point exceeding 42° C., the crosslinked shape memory polymer becomes poor in shape memory ability, exhibiting a deformation recovery rate of 90% or less.

Specifically, after being crosslinked, the shape memory polymer of the present invention exhibits a deformation recovery rate of 90% at a temperature of 28 to 42° C. including the human body temperature, thus finding various applications in physiomedical application devices, such as a nasolacrimal duct insertion member, or medical materials.

The shape memory polymer may be a biodegradable shape memory polymer. More specifically, "biodegradable shape memory polymer", which is defined as a substance that is degradable and absorbed into the human body over time and can change its shape according to temperature changes, means a polymer that changes in shape with temperature and undergoes degradation and absorption into the body. For example, the biodegradable shape memory polymer may be a biodegradable shape memory polymer irrespective of whether it is crosslinked or not.

Particularly, a nasolacrimal duct insertion member according to an embodiment of the present invention is made of a biodegradable shape memory polymer so that external deformation of the nasolacrimal duct insertion member rather than physical deformation of the human nasolacrimal duct is possible, thus minimizing various factors, caused by physical deformation of the nasolacrimal duct, which have adverse effects on the flow of tears. Moreover, when applied to the human body, the nasolacrimal duct insertion member composed of substances that can remain semi-permanently in the body is advantageous because a post-operative procedure of removing the insertion member can be omitted.

The shape memory polymer represented by Chemical Formula 1 may be prepared using a method comprising a step of reacting a compound of Chemical Formula 3, a compound of Chemical Formula 4, and a compound of Chemical Formula 4 into the shape memory polymer of Chemical Formula 1, but without limitations thereto.

[Chemical Formula 3]

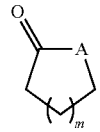

[Chemical Formula 4]

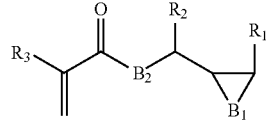

[Chemical Formula 5]

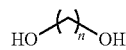

wherein, $R_1$, $R_2$, and $R_3$ are each independently hydrogen (H) or an alkyl ($C_nH_{2n+1}$—) of 1 to 6 carbon atoms, m and n are each an integer of 1 to 20, and A, $B_1$, and $B_2$ are each independently oxygen (O) or sulfur (S), As described above, the shape memory polymer according to the present disclosure may have a structure of a polymer in which ε-caprolactone monomers and glycidyl-bearing acryl monomers are polymerized. By way of example, the shape memory polymer may have a structure of [PCL-co-PGMA)] copolymer in which ε-caprolactone monomers (CL; caprolactone) and glycidyl methacrylate (GMA) are polymerized.

In this regard, the compound of Chemical Formula 5 may be an initiator for polymerization. For example, 1,6-hexanediol may be an initiator. Particularly for the polymerization, the compound of Chemical Formula 3 and the compound of Chemical Formula 4 may be subjected to condensation polymerization on the basis of the compound of Chemical Formula 5 and may be arranged in alternating, random, or block patterns with respect to the compound of Chemical Formula 5.

In an embodiment, a method for preparing a shape memory polymer having the structure of copolymer [PCL-co-PGMA] may comprising mixing ε-caprolactone (CL) and glycidyl methacrylate (GMA) monomers at a proper molar ratio and reacting the same at a reaction temperature of 80 to 140° C. in the presence of a catalytic compound.

When the reaction mixture is determined to be thermally stable, an initiator is added to perform a copolymerization reaction, followed by purification through washing and filtration and then drying to afford the shape memory polymer of Chemical Formula 1.

In an embodiment according to the present invention, the mechanism of polymerization to the shape memory polymer of PCL-co-PGMA is illustrated as follows:

C. on average. In greater detail, when polymer synthesis is conducted at less than 100° C., no catalytic reaction may be achieved. Polymer synthesis at higher than 130° C. may lower the rate of the catalytic reaction.

Such a shape memory polymer is subjected to crosslinking. Crosslinking is to maintain the shape memory polymer in a stable form. In detail, the crosslinking may refer to chemical crosslinking. In a crosslinked polymer, the individual polymer chains are linked via covalent bonds, so that the shape memory polymer can be maintained in a stable form when crosslinked.

The crosslinking, which is adapted to maintain the shape memory polymer in a stable form, may confer an initial shape (the shape to which the polymer returns) on the shape

[Reaction Scheme 1]

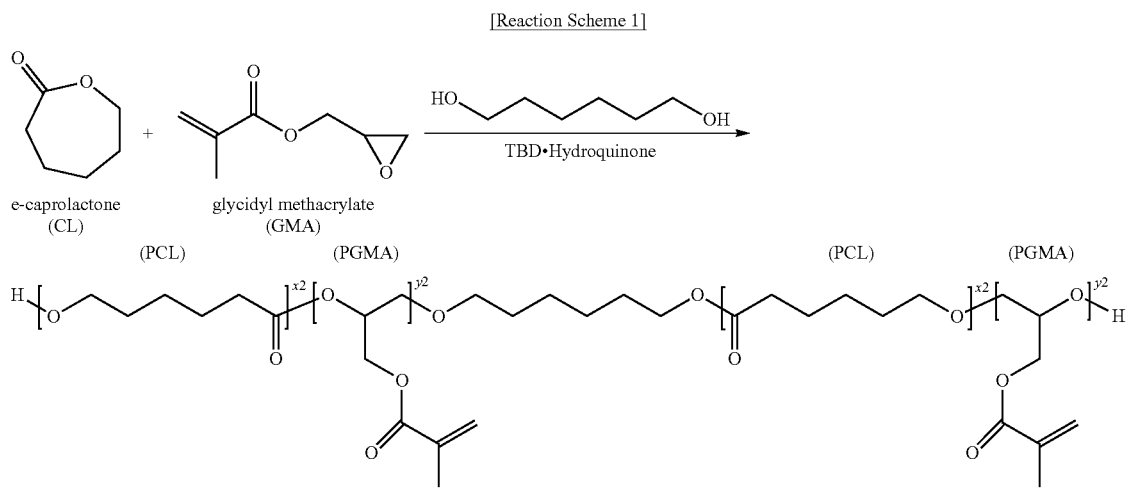

As stated above, the method for preparing a shape memory polymer according to an embodiment of the present invention comprises a step of copolymerizing ε-caprolactone (CL) and glycidyl methacrylate (GMA) monomers.

In addition, the catalyst may be 1,5,7-triazabicyclo[4.4.0]dec-5-ene (TBD), tin (II) (2-ethylhexanoate), trimethylopropane tris(3-mercaptopropionate), or zinc succinate. TBD may be used as a catalyst because it guarantees high yield even when used in a small amount.

The amount of the catalyst is not limited, but may be preferably 0.5 to 1 mole relative to the starting materials.

Particularly, 1,5,7-triazabicyclo[4.4.0]dec-5-ene (TBD) is to induce the simultaneous ring-opening polymerization of the two monomers (CL and GMA), thus enjoying the advantage of reducing the synthesis time of a shape memory polymer.

At a point of time at which almost no polymerization conversion rate is obtained, that is, at an initial reaction time, a polymerization inhibitor may be fed, together with an HD initiator, prior to the addition of the GMA monomers, so that the temperature-sensitive GMA acryl groups can be reacted with each other.

Moreover, the polymerization inhibitor plays a role in terminating the reaction by suppressing exothermic reactions occurring locally at a late polymerization stage and scavenging unreacted remaining radicals and may include, but is not limited to, at least one selected from the group consisting of hydroquinone (HQ), hydroquinone monomethyl ether, p-benzoquinone, and phenothiazine.

In this regard, the step of synthesizing the shape memory polymer may be performed at 80 to 140° C. or 100 to 130° memory polymer. That is, crosslinking may be performed at the time when an initial shape is conferred on the shape memory polymer, but not upon synthesis thereof. For example, in order to manufacture a nasolacrimal duct insertion member, a shape memory polymer is dissolved and the polymer solution is poured into a mold, wherein a crosslinker may be added upon dissolution of the shape memory polymer and used to induce a crosslinking reaction in the mold.

Particularly, a photo-crosslinking reaction may be induced in the synthesized shape memory polymer to further lower the melting point. For example, when induced by ultraviolet (UV) light with a wavelength of 320 to 500 nm, the crosslinking may decrease the melting point of the shape memory polymer to 28 to 42° C. For example, 320-500 nm ultraviolet (UV) light may be applied to the shape memory polymer of Chemical Formula 1. When exposed to the light, the functional group glycidyl included in Chemical Formula 1 may form a covalent form with an adjacent glycidyl group.

Moreover, an aspect of the present invention provides a nasolacrimal duct insertion member comprising the shape memory polymer described above. Hereinafter, a nasolacrimal duct insertion member according to an embodiment will be described in detail with reference to FIGS. 2 to 4.

Figure 2:
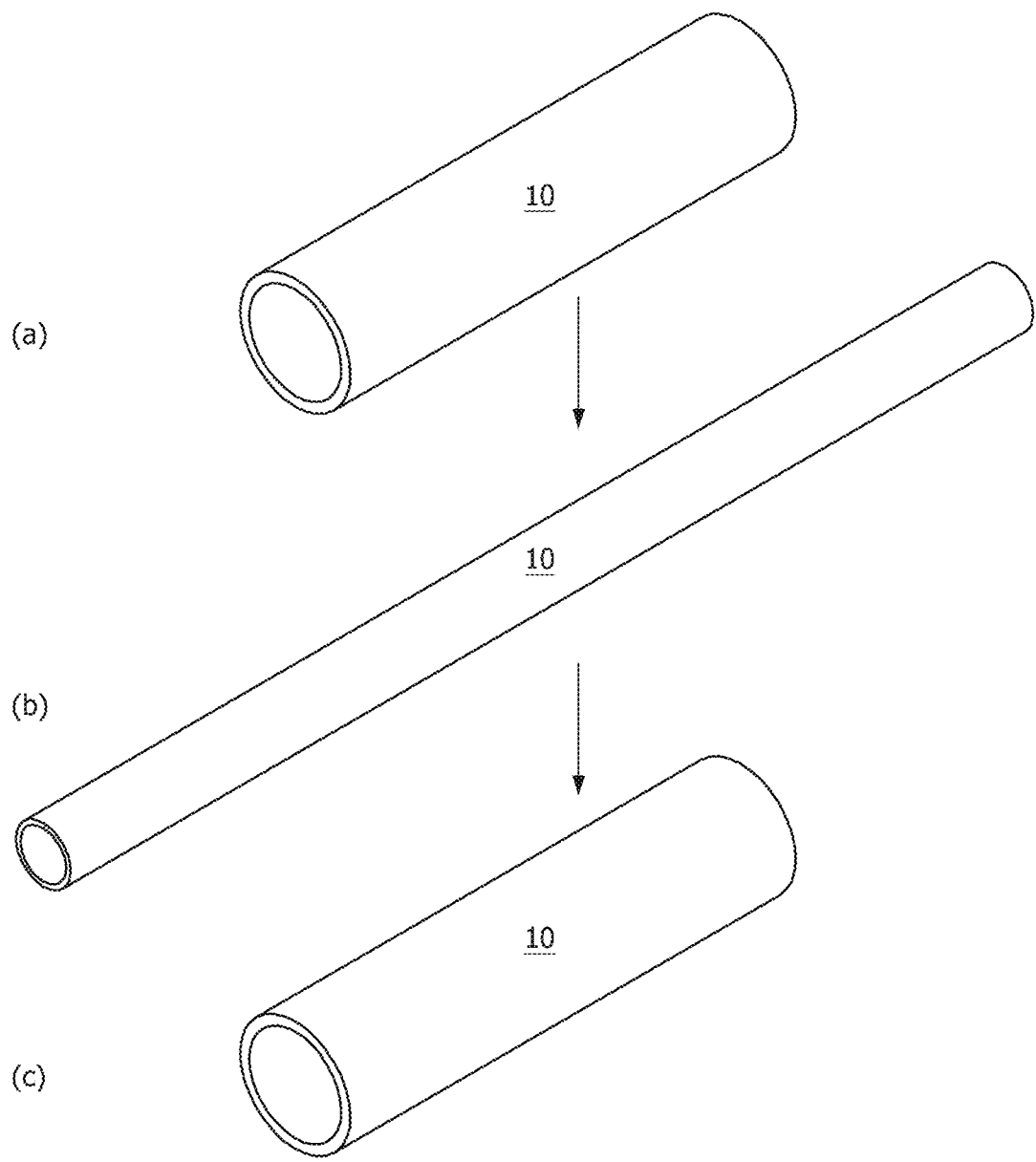
FIG. 2 is a view showing a process in which a nasolacrimal duct insertion member according to the present invention undergoes shape changes ((a) initial shape, (b) temporary shape (deformed shape), and (c) permanent shape (recovered shape)).
Figure 3:
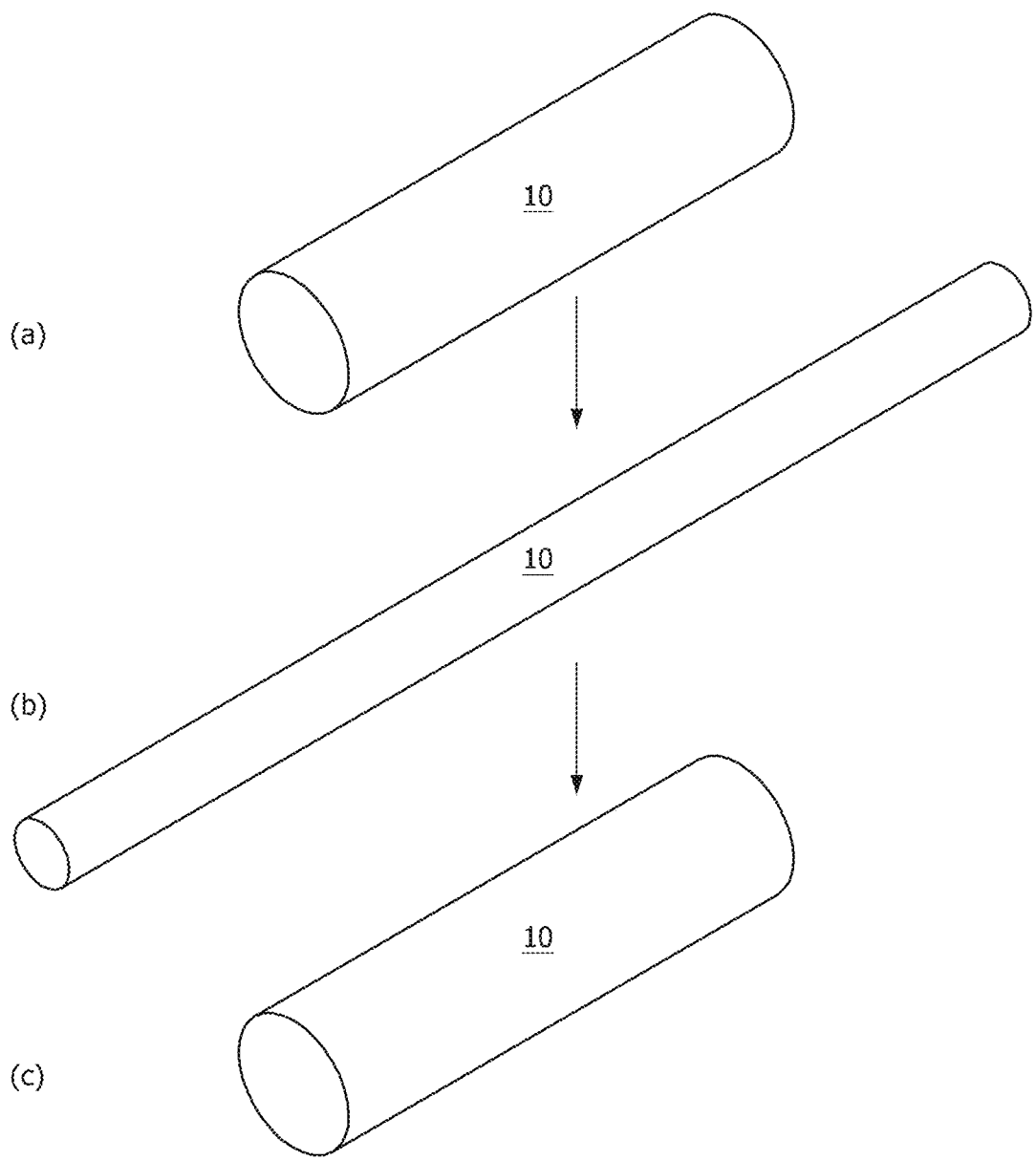
FIG. 3 is a view showing a process in which a nasolacrimal duct insertion member according to the present invention undergoes shape changes ((a) initial shape, (b) temporary shape (deformed shape), and (c) permanent shape (recovered shape)).
Figure 4:
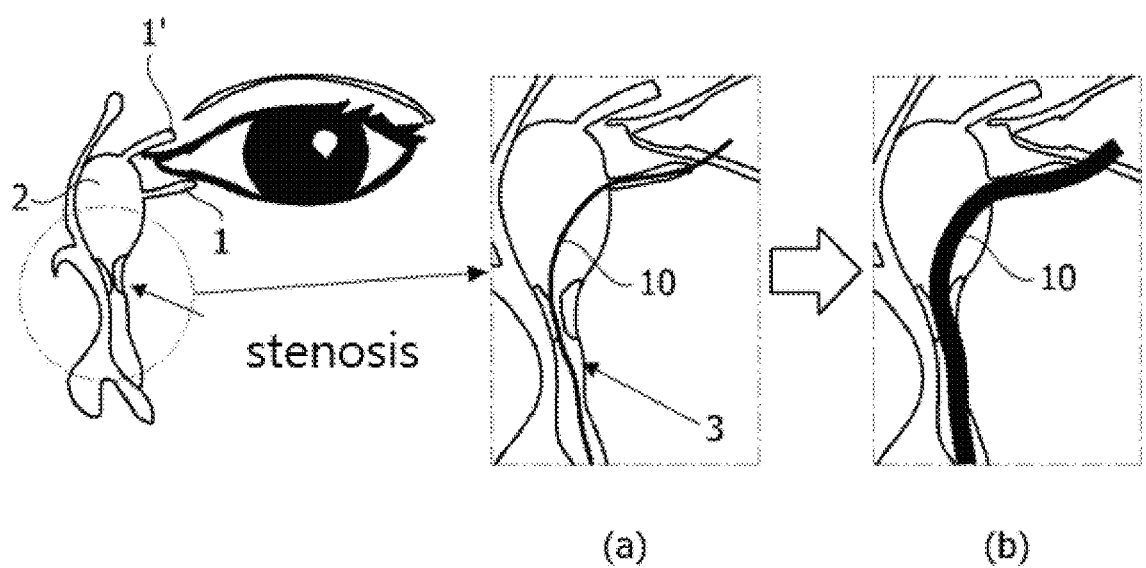
FIG. 4 is a view showing an embodiment in which a nasolacrimal duct insertion member according to the present invention is applied to the human body ((a) temporary shape (deformed) and (b) permanent shape (recovered)).
Figure 5:
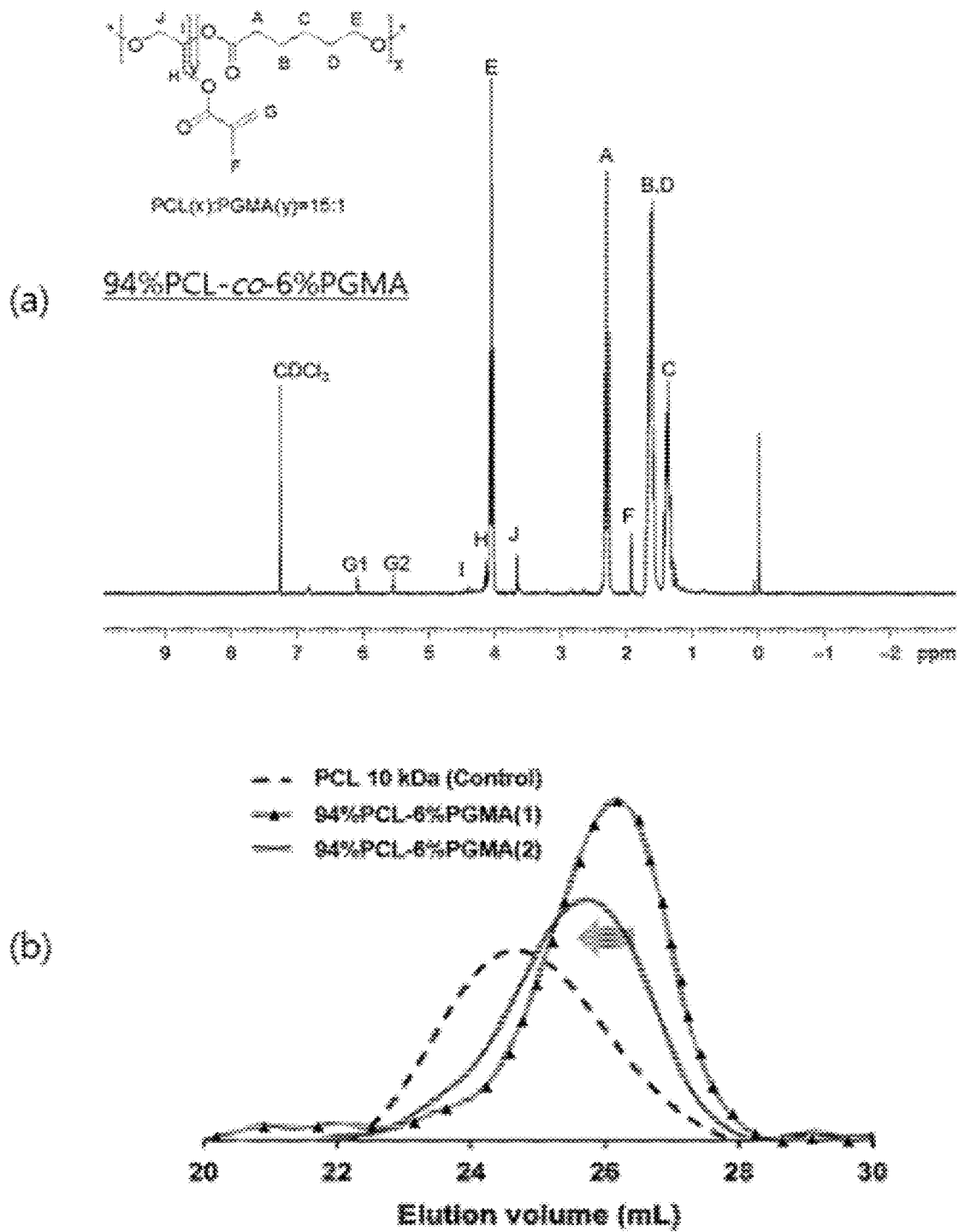
FIG. 5 is a view showing the results of $^1$H NMR spectrum and GPC analysis of a shape-memory polymer prepared in Example 1-1 of the present invention (94% PCL-co-6% PGMA).

FIGS. 2 and 3 are views showing a shape change process of a nasolacrimal duct insertion member according to the present invention ((a) initial shape, (b) temporary shape (deformed), and (c) permanent shape (recovered state)), and FIG. 4 is a view showing an embodiment in which a nasolacrimal duct insertion member according to the present invention is applied to the human body ((a) temporary shape (deformed) and (b) permanent shape (recovered)).

With reference to FIGS. 2 and 3, a nasolacrimal duct insertion member (10) according to the present invention is inserted into a nasolacrimal duct (3) and may be in the form of a tube. For example, the nasolacrimal duct insertion member may be in a tubular form with both ends open (FIG. 2) or with the inside blocked (FIG. 3).

In an embodiment, the nasolacrimal duct insertion member (10) with both ends open can be applied to the inside of an obstructed or narrowed nasolacrimal duct and expand the inside of the nasolacrimal duct, thereby easily discharging tears (FIG. 2).

In another embodiment, the tube-like nasolacrimal duct insertion member with the inside blocked can expand the inside of the nasolacrimal duct and allow the discharge of tears along the outer surface of the nasolacrimal duct insertion member. Alternatively, the discharge of tears can be suppressed through the inside of the tube, and the amount of tears to be discharged can be controlled by changing the diameter of the inside of the tube (FIG. 3).

The nasolacrimal duct insertion member (10) may be in the form of a tube and is made of a shape memory polymer, so that the shape can be deformed according to the inner diameter of the nasolacrimal duct (3) at an average temperature of 28 to 42° C. or higher and maintain an average diameter of 0.4 to 1.2 mm at an average temperature of 28 to 42° C. or higher. For example, the shape memory polymer may range in melting point from 28 to 42° C., 30 to 41° C., 32 to 40° C., 34 to 39° C. or 36 to 37° C., and can change in shape at a temperature higher than the melting point. In detail, the shape change may be modified depending on the shape of the nasolacrimal duct (3). That is, the member may maintain a diameter of 0.4 to 1.2 mm, 0.5 to 1.0 mm, 0.6 to 0.9 mm, or 0.7 to 0.8 mm at higher than the melting point range. However, deformation may be performed at a temperature of 28 to 42° C. or higher, but the deformation temperature should not exceed 50° C., which is a protein denaturation temperature. For example, the temperature at which the shape memory polymer is deformed may be in the range of 28 to 42° C., or may be higher than the upper limit, but less than 50° C.

In greater detail, the nasolacrimal duct insertion member, which is made of a shape memory polymer of Chemical Formula 1, can be fixedly fitted to the inner diameter of the nasolacrimal duct to which the member is applied as the member returns to the initial shape at 28 to 42° C. or higher from a temporary shape deformed by a physical force, whereby the narrowed or obstructed nasolacrimal duct can be expanded. Here, the physical force may refer to an external stimulus for inducing a change from the initial shape to the temporary shape, and may be a stimulus such as temperature, light, etc., or a mechanical force at a melting point or higher.

Designed to return to an initial shape at a temperature of 28 to 42° C. or higher, the nasolacrimal duct insertion member induces a spontaneous shape change in the human body when applied inside the human body. That is, it is designed to guarantee a spontaneous shape change at around the body temperature, that is, 36 to 38° C.

The nasolacrimal duct insertion member (10) according to an embodiment of the present invention may be a biodegradable shape memory polymer.

More specifically, as described above, "biodegradable shape memory polymer", which is defined as a substance that is degradable and absorbed into the human body over time and can change its shape according to temperature changes, means a polymer that changes in shape with temperature and undergoes degradation and absorption into the body.

Particularly, the nasolacrimal duct insertion member (10) according to an embodiment of the present invention is made of a biodegradable shape memory polymer so that external deformation of the nasolacrimal duct insertion member rather than physical deformation of the human nasolacrimal duct (3) is possible, thus minimizing various factors, caused by physical deformation of the nasolacrimal duct, which have adverse effects on the flow of tears. Moreover, when applied to the human body, the nasolacrimal duct insertion member (10) composed of substances that can remain semi-permanently in the body is advantageous because a post-operative procedure of removing the insertion member (10) can be omitted.

When applied to the stenosis site of the nasolacrimal duct (3), the nasolacrimal duct insertion member (10) containing the biodegradable shape memory polymer can expand the damage site (stenosis or obstructed site) of the nasolacrimal duct (3) without inflammation, a damage in the nasolacrimal duct epithelial cells, or a foreign body reaction and exhibits an improved biodegradable and regeneration effect to open the obstructed or narrowed nasolacrimal duct (3).

In addition, the present invention provides a method for manufacturing a nasolacrimal duct insertion member comprising a shape memory polymer. For example, the nasolacrimal duct insertion member may be in the form of a tube, and can be manufactured using a tube-shaped mold. More specifically, the nasolacrimal duct insertion member may be manufactured by dissolving the shape memory polymer of Formula 1 and an initiator in a solvent, pouring the solution into a tube-shaped mold and crosslinking the same. The mold may be made of glass or PDMS material, which is to increase light transmittance for crosslinking.

In this regard, the reaction may be conducted at room temperature. For example, the reactants may be reacted at 15 to 25° C., 17 to 23° C., 19 to 21° C., or 20° C. If the reaction temperature exceeds the upper limit, air bubbles may be generated, giving an unpredicted porous structure to the resulting nasolacrimal duct insertion member. A chiller may be used to lower the temperature.

The solvent used may be at least one selected from the group consisting of diethyl ether, chloroform, 1,4-dioxane, dichloromethane, ethyl acetate, tetrahydrofuran, acetone, acetonitrile, N,N-dimethylformamide, N,N-dimethylacetamide, N-methylpyrrolidone, dimethylsulfoxide, acetonitrile, methyl ethyl ketone, and diethyl ketone.

The initiator may be a photoinitiator, which creates a radical upon exposure to UV radiation, and may be selected from the group consisting of DMPA (2,2-dimethoxy-2-phenylacetonephenone), HOMPP (2-hydroxy-2-methylpropipphenone), LAP (lithium phenyl-2,4,6-trimethylbenzoylphosphinate), and IRGACURE 2959 (1-[4-(2-Hydroxyethoxy)-phenyl]-2-hydroxy-2-methyl-1-propane-1-one), which can all be utilized in an aqueous solution, but with no limitations thereto. The initiator may be contained in an amount of 0.1 to 0.5 w/v %, 0.2 to 0.4 w/v %, or 0.3 w/v %, based on the volume of the solvent. When the concentration of the photoinitiator is too low, the photopolymerization is not effectively conducted. The characteristics of a shape memory polymer may be observed to lose at too high a concentration of the photoinitiator.

In addition, the shape memory polymer may be contained in an amount of 30 to 300 w/v %, 30 to 270 w/v %, 35 to 240 w/v %, 40 to 210 w/v %, 45 to 170 w/v %, 50 to 140 w/v %, 50 to 100 w/v %, 65 to 90 w/v %, or 75 w/v %, based on the volume of the solvent.

Hereinafter, processes in which the nasolacrimal duct insertion member in a tube form undergoes a shape change and is inserted into the nasolacrimal duct will be explained. First, when the nasolacrimal duct insertion member with the original shape (FIG. 2(a)) is stretched at less than the melting point by applying physical force (tension) in opposite directions, the member extends in the lengthwise direction, with the concomitant decrease of the outer diameter, and thus is deformed into a temporary shape to be inserted into the nasolacrimal duct (FIG. 2(b)). For reference, the nasolacrimal duct insertion member may be inserted through the lacrimal punctum.

After being inserted into the nasolacrimal duct, the nasolacrimal duct insertion member maintained in the temporary form returns to the initial shape before physical force-induced deformation (before tension application) and thus can maintain the permanent shape as the temperature is gradually elevated to the transition temperature (about 28 to 42° C.). That is, the nasolacrimal duct insertion member is contracted in the lengthwise direction within the nasolacrimal duct, with the concomitant increase of the outer diameter, so that the outer peripheral surface of the nasolacrimal duct insertion member becomes in close contact with the nasolacrimal duct and is fixedly maintained with the permanent shape. Thus, insertion can be made of the nasolacrimal duct insertion member.

The term "strain rate", as used in the context of a shape memory polymer, refers to a rate of shape change when a polymer is restored from a temporary shape to an initial shape and maintains a permanent shape, accounting for a rate of change from a temporary shape to a permanent shape. The term "deformation recovery rate" means a recovery ratio of the initial shape before deformation by a physical force from a temporary shape, describing a ratio of the permanent shape to the initial shape. In the present invention, the strain rate may vary depending on the ratio or conditions (temperature, UV, etc.) of the monomers included in the shape memory polymer, and may be specifically 5 to 350%. In addition, the deformation recovery rate may be 90% or more.

At an average temperature of 28 to 42° C. or higher, the nasolacrimal duct insertion member in a permanent shape may range in length from 10 to 50 mm, 15 to 45 mm, 20 to 40 mm, or 25 to 30 mm. In addition, the inner diameter of the nasolacrimal duct insertion member may be 0.2 to 0.7 mm before implantation into the nasolacrimal duct and may increases to 0.4 to 1.2 mm at an average temperature of 28 to 42° C. or higher after implantation. For example, the inner diameter of the nasolacrimal duct insertion member may be 0.5 mm before being implanted into the nasolacrimal duct and may increase to 1.0 mm before implantation. A degree of change can be adjusted by controlling the composition of the polymer, crosslinking duration, UV energy for crosslinking, etc.

In addition, at an average temperature of 28 to 42° C. or higher, the cross-sectional thickness of the nasolacrimal duct insertion member may be 50 to 200 μm, and preferably 100 to 200 μm, or 100 μm. For example, the nasolacrimal duct insertion member set to have a cross-sectional thickness in the above range can smoothly discharge lacrimal fluid (tears).

Furthermore, the strength (Young's modulus), the degree of crosslinking, the melting point, etc. of the nasolacrimal duct insertion member can be controlled by adjusting the weight ratio of the above-described shape memory polymer to the volume of the solvent upon manufacture of the nasolacrimal duct insertion member.

Specifically, the strength may be 0.039 to 0.317 MPa, 0.1 to 0.3 MPa, 0.15 to 0.25 MPa, or 0.17 to 0.2 MPa when the shape memory polymer is controlled to 50 to 100 w/v % relative to the solvent. For example, the nasolacrimal duct insertion member preferably has a strength 0.03 to 0.3 MPa, and when the shape memory polymer is used in an amount of 50 to 200 w/v %, the strength can be maintained.

Proposed as a structure to change in shape depending on the inner diameter of the nasolacrimal duct, as described above, the nasolacrimal duct insertion member according to an embodiment of the present invention is much simpler and more convenient in insertion into the nasolacrimal duct than conventional members. In addition to shortening the operation time, the nasolacrimal duct insertion member enjoys the advantages of reducing mistakes that might occur during the insertion procedure and thus improving the surgical stability.

Hereinafter, the present invention will be described in more detail by the following Examples and Experimental Examples.

However, the following Examples and Experimental Examples are merely illustrative of the present invention, but are not intended to limit the present invention.

<Preparations for Experiments>

1. Samples and Devices

ε-Caprolactone (CL), hydroquinone (HQ), 1,5,7-triazabicyclo[4.4.0]dec-5-ene (TBD), glycidyl methacrylate (GMA), acetonitrile, chloroform, dichloromethane, diethyl ether, 2,2-dimethoxy-2-phenylacetophenone, and 1,6-hexanediol (HD) were purchased from Sigma-Aldrich.

The melting point and the heat of fusion were measured from a mass of a sample ranging from 5 to 10 mg in an aluminum pan using differential scanning calorimetry (DSC) equipment commercially available from TA Instrument Inc. Then, the rate of a lamp was 10° C./min, and measured once at a temperature ranging from −80° C. to 100° C. (including a constant temperature for 3 minutes).

In addition, the number-average molecular weight ($M_n$) was measured using gel permeation chromatography (GPC) equipment, commercially available from Shimadzu Scientific Instruments Inc., with the columns Shodex 802, 803, and 804. Chloroform was used as a solvent at a flow rate of 1.0 mL/min.

Also, the polymer UV crosslinking was determined using UV/visible ray crosslinking equipment, commercially available from Lumen Dynamics Group Inc., at an intensity of 14 W/cm$^2$ for 10 min.

Example 1. Synthesis of PCL-Co-PGMA Shape Memory Polymer 1-1. Synthesis of 94% PCL-Co-6% PGMA 1-1-1. Synthesis of 94% PCL-Co-6% PGMA At the reactant input ratio of $[CL]_0/[GMA]_0/[HD]_0/[TBD]_0/[HQ]_0$=90/10/1/1/0.5, 94% PCL-co-6% PGMA was synthesized as follows (see Table 1).

TABLE 1

| | CL (mmol) | GMA (mmol) | HQ (mmol) | TBD (mmol) | HD (mmol) |
|---|---|---|---|---|---|
| Example 1-1-1 | 90 | 10 | 1 | 1 | 0.5 |

First, CL (90 mmol, 9.97 mL), HD (0.5 mmol, 60 mg), and HQ (1 mmol, 110 mg) were put into a glass reactor (250 mL) and mixed for 10 min, followed by GMA (10 mmol, 1.36 mL).

Then, when the inner temperature of the glass reactor having the two monomers mixed therein was judged to be thermally stable, TBD (1 mmol, 140 mg), as a catalyst for inducing the simultaneous ring-opening polymerization of CL and GMA, was dissolved in 1 mL of acetonitrile and the solution was added to the glass reactor and stirred at 110° C. for 2 hours. The entire procedure was performed under high-purity nitrogen.

After the reaction, 5 g of the reaction mixture was dissolved in 10 mL of chloroform and slowly added dropwise to diethyl ether (400 mL) to form precipitates. Then, the precipitates were filtered through a filter paper and the solvent was removed using a rotary evaporator. The precipitates were dried at a reduced pressure to afford a PCL-co-PGMA polymer.

The components of the synthesized polymer (the ratio of PCL and PGMA repeat units in terms of the ratio of hydrogen atoms in the PCL and PGMA) were measured using $^1$H NMR (nuclear magnetic resonance). The measurement results are shown in FIG. 10($a$).

Figure 10:
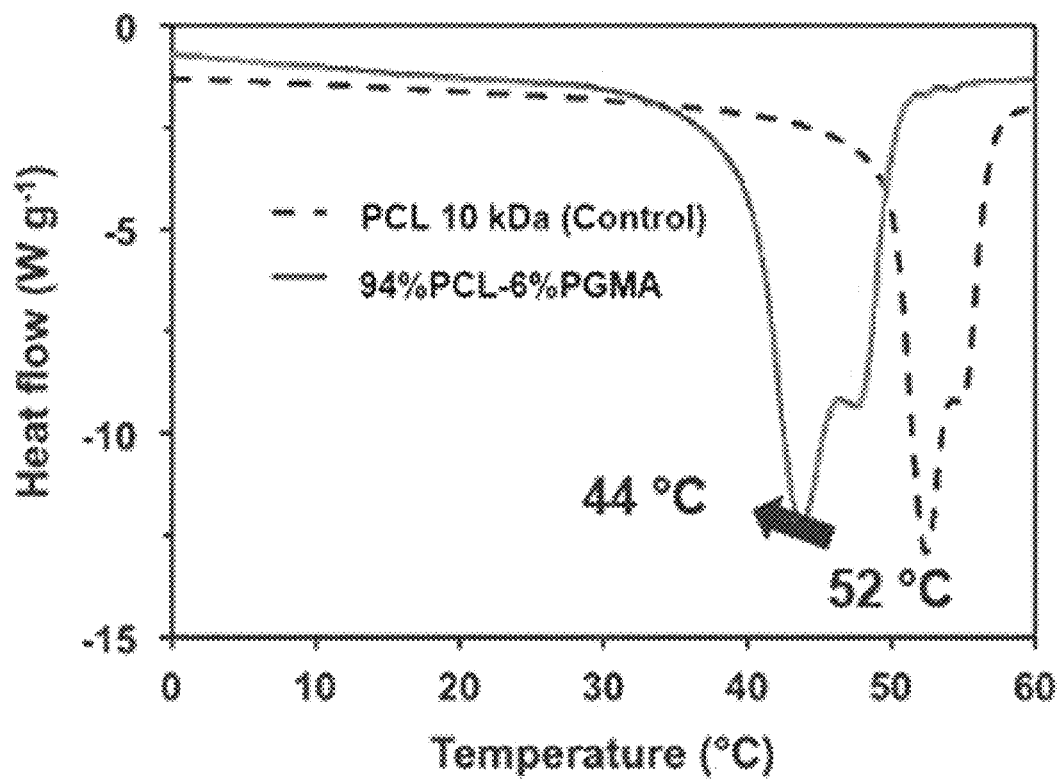
FIG. 10 shows DSC profiles of the polymers of Example 1-1 and Comparative Example 1 prepared in the present invention.

Referring to FIG. 10($a$), the repeat unit ratio (%) of PCL and PGMA repeat units (PCL:PGMA=15:1) was calculated by $^1$H NMR analysis based on the chemical structure of the synthetic polymer. In Example 1-1-1, 94% PCL-co-6% PGMA was identified.

Turning to FIG. 10($b$), the molecular weight of the 94% PCL-co-6% PGMA (1-HD 0.5 mmol, 2-HD 0.25 mmol) polymer was found to have a molecular weight (Mw) below the desired Mw level of 10 kDa, as analyzed by GPC. The molecular weight might be easily controlled by adjusting the amount of the initiator added.

1-1-2. Synthesis of 94% PCL-Co-6% PGMA

The same polymerization procedure as in Example 1-1-1 was carried out, with the exception that 7.5 g of the reaction mixture after the reaction was dissolved in 10 ml of chloroform.

1-1-3. Synthesis of 94% PCL-Co-6% PGMA

The same polymerization procedure as in Example 1-1-1 was carried out, with the exception that 10 g of the reaction mixture after the reaction was dissolved in 10 ml of chloroform.

1-2. Synthesis of 92% PCL-Co-8% PGMA

At the reactant input ratio of $[CL]_0/[GMA]_0/[HD]_0/[TBD]_0/[HQ]_0$=86/14/1.4/1/0.5, 92% PCL-co-8% PGMA was synthesized as follows (see Table 2).

TABLE 2

|  | CL (mmol) | GMA (mmol) | HQ (mmol) | TBD (mmol) | HD (mmol) |
|---|---|---|---|---|---|
| Example 1-2 | 86 | 14 | 1.4 | 1 | 0.5 |

Polymerization was performed in the same manner as in Example 1-1-1.

The components of the synthesized polymer (the ratio of PCL and PGMA repeat units in terms of the ratio of hydrogen atoms in the PCL and PGMA) were measured using $^1$H NMR (nuclear magnetic resonance). The measurement results are shown in FIG. 6.

Figure 6:
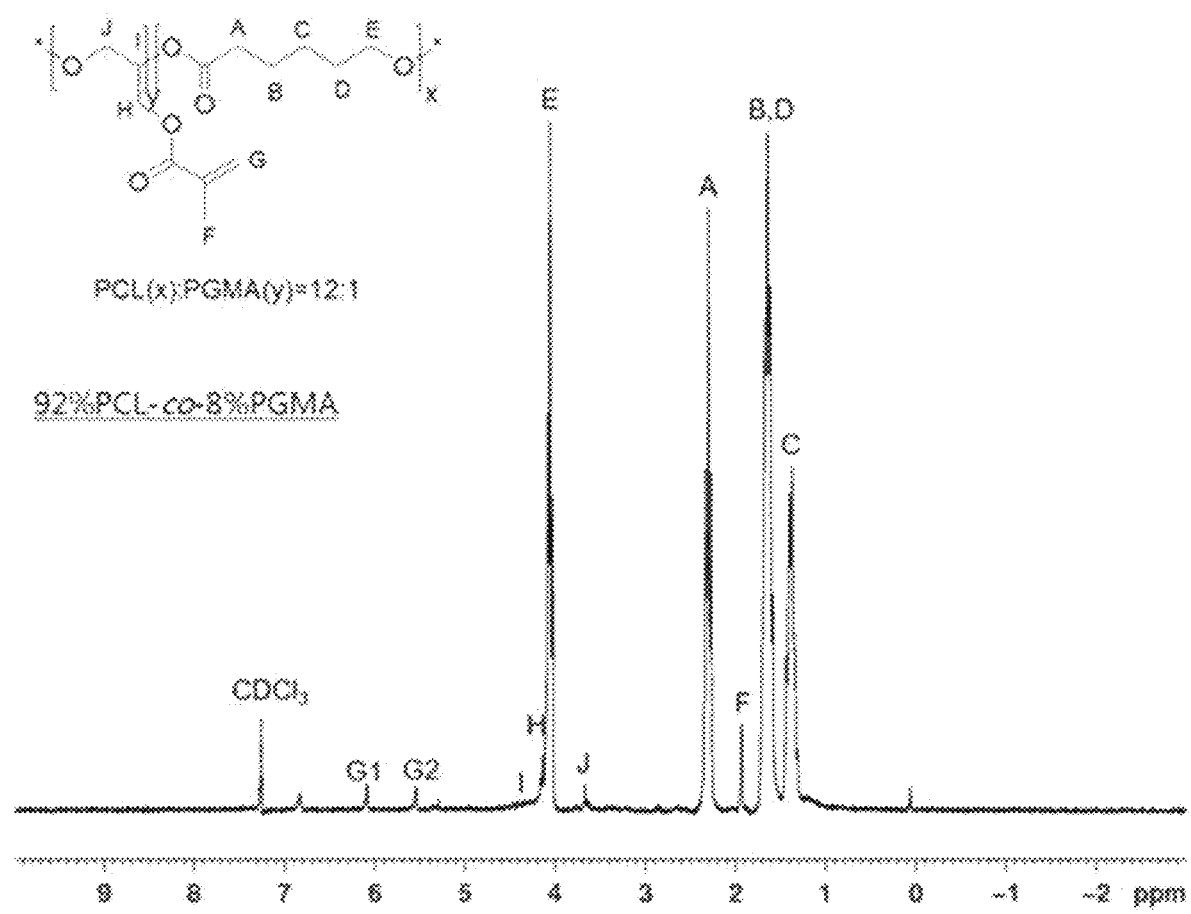
FIG. 6 is a view showing the $^1$H NMR spectrum of a shape-memory polymer prepared in Example 1-2 of the present invention (92% PCL-co-8% PGMA).

With reference to FIG. 6, the repeat unit percentage (%) of the PCL and PGMA repeat unit ratio (PCL:PGMA=12:1) was calculated through $^1$H NMR analysis. The repeat unit percentage in the polymer of Example 1-2 was measured to be 92% PCL-co-8% PGMA.

1-3. Synthesis of 90% PCL-Co-10% PGMA

At the reactant input ratio of $[CL]_0/[GMA]_0/[HD]_0/[TBD]_0/[HQ]_0$=82/18/1.8/1/0.5, 90% PCL-co-10% PGMA was synthesized as follows (see Table 3).

TABLE 3

|  | CL (mmol) | GMA (mmol) | HQ (mmol) | TBD (mmol) | HD (mmol) |
|---|---|---|---|---|---|
| Example 1-3 | 82 | 18 | 1.8 | 1 | 0.5 |

Polymerization was performed in the same manner as in Example 1-1-1.

The components of the synthesized polymer (the ratio of PCL and PGMA repeat units in terms of the ratio of hydrogen atoms in the PCL and PGMA) were measured using $^1$H NMR (nuclear magnetic resonance). The measurement results are shown in FIG. 7.

Figure 7:
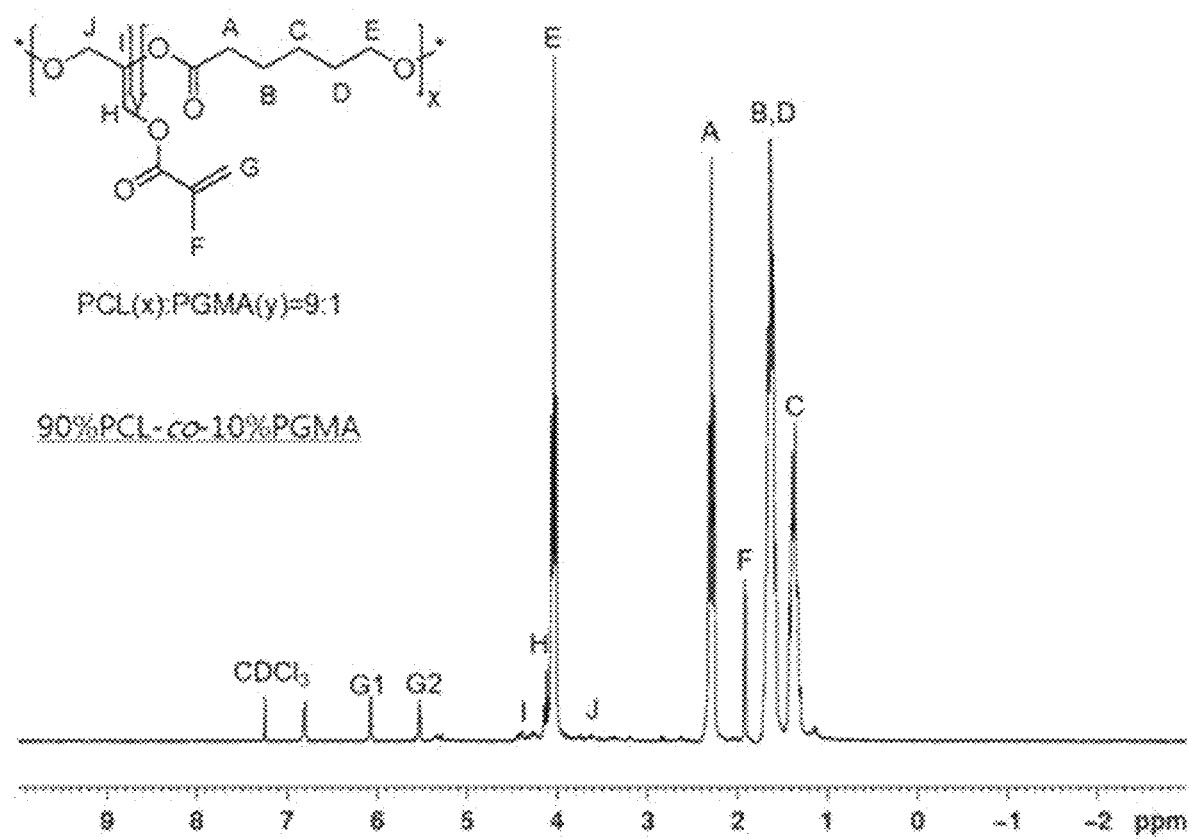
FIG. 7 is a view showing the $^1$H NMR spectrum of a shape-memory polymer prepared in Example 1-3 of the present invention (90% PCL-co-10% PGMA).

With reference to FIG. 7, the repeat unit percentage (%) of the PCL and PGMA repeat unit ratio (PCL:PGMA=9:1) was calculated through $^1$H NMR analysis. The repeat unit percentage in the polymer of Example 1-3 was measured to be 90% PCL-co-10% PGMA.

1-4. Synthesis of 88% PCL-Co-12% PGMA

At the reactant input ratio of $[CL]_0/[GMA]_0/[HD]_0/[TBD]_0/[HQ]_0$=78/22/2.2/1/0.5, 88% PCL-co-12% PGMA was synthesized as follows (see Table 4).

TABLE 4

|  | CL (mmol) | GMA (mmol) | HQ (mmol) | TBD (mmol) | HD (mmol) |
|---|---|---|---|---|---|
| Example 1-4 | 78 | 22 | 2.2 | 1 | 0.5 |

Polymerization was performed in the same manner as in Example 1-1-1.

The components of the synthesized polymer (the ratio of PCL and PGMA repeat units in terms of the ratio of hydrogen atoms in the PCL and PGMA) were measured using $^1$H NMR (nuclear magnetic resonance). The measurement results are shown in FIG. 8.

Figure 8:
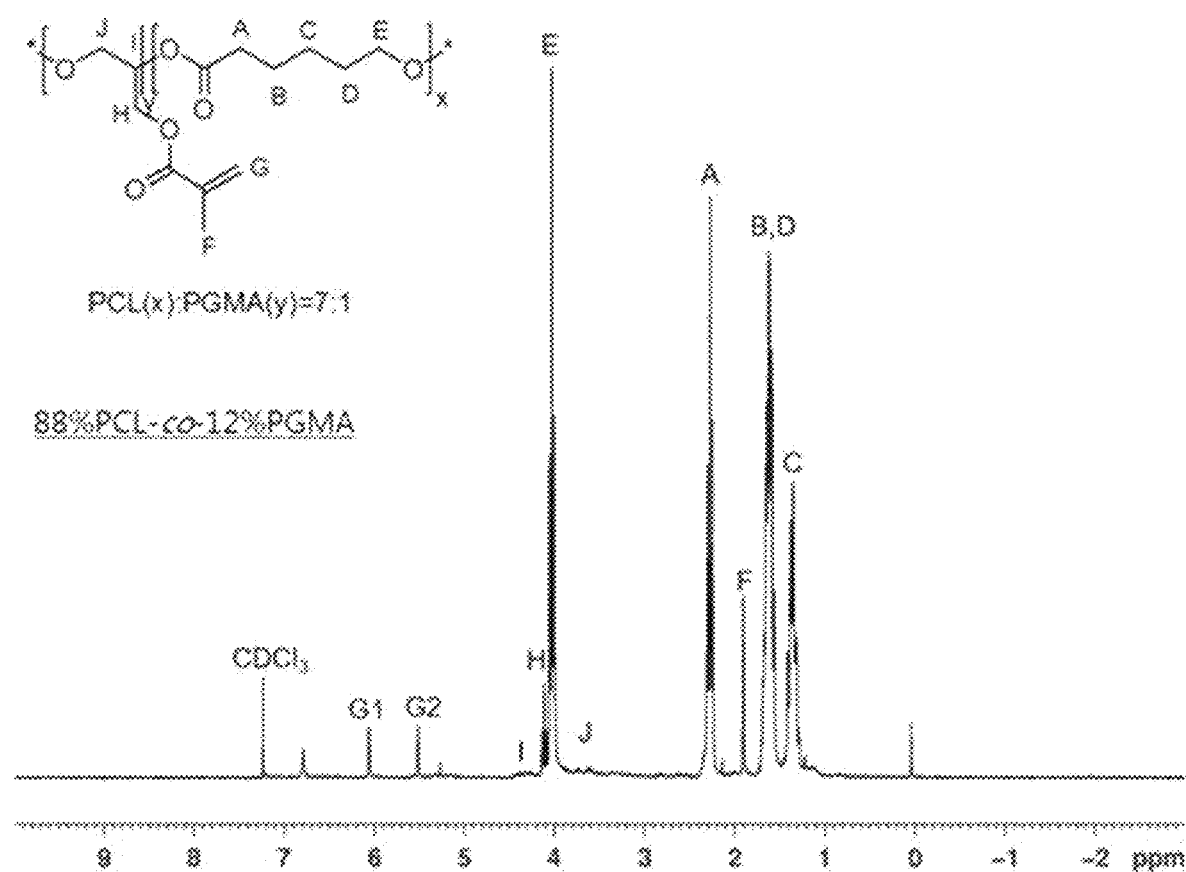
FIG. 8 is a view showing the $^1$H NMR spectrum of a shape-memory polymer prepared in Example 1-4 of the present invention (88% PCL-co-12% PGMA).

With reference to FIG. 8, the repeat unit percentage (%) of the PCL and PGMA repeat unit ratio (PCL:PGMA=7:1) was calculated through $^1$H NMR analysis. The repeat unit percentage in the polymer of Example 1-4 was measured to be 88% PCL-co-12% PGMA.

Example 2. Synthesis of PCL-Co-PGMA Shape Memory Polymer

Polymers were synthesized at the following $[CL]_0/[GMA]_0/[HD]_0/[TBD]_0/[HQ]_0$ ratios (Examples 2-1 to 2-4).

TABLE 5

|  | CL (mmol) | GMA (mmol) | HQ (mmol) | TBD (mmol) | HD (mmol) |
|---|---|---|---|---|---|
| Example 2-1 | 90 | 10 | 1 | 0.5 | 0.5 |
| Example 2-2 | 86 | 14 | 1.4 | 0.5 | 0.5 |
| Example 2-3 | 82 | 18 | 1.8 | 0.5 | 0.5 |
| Example 2-4 | 78 | 22 | 2.2 | 0.5 | 0.5 |

Briefly, CL, HD, and HQ were put into a glass reactor (250 mL) and mixed for 10 min, followed by GMA in Examples 2-1 to 2-4 (see Table 5).

Then, when the inner temperature of the glass reactor having the two monomers mixed therein was judged to be thermally stable, TBD (1 mmol, 140 mg), as a catalyst for inducing the simultaneous ring-opening polymerization of CL and GMA, was dissolved in 1 mL of acetonitrile and the solution was added to the glass reactor and stirred at 110° C. for 2 hours. The subsequent procedure was performed in the same manner as in Examples 1-1-1.

The polymers synthesized in Examples 2-1 to 2-4 were exposed to UV light (320-500 nm) at the intensity of 14 W/cm$^2$ for 10 min to afford shape memory polymers applicable to the human body.

Example 3. Manufacture of Nasolacrimal Duct Insertion Member for Opening Obstructed Nasolacrimal Duct A nasolacrimal duct insertion member was manufactured using the polymer prepared in Example 1-1-1.

For use in manufacturing a tubular nasolacrimal duct insertion member, a tube-shaped mold was prepared to have an inner/outer wall structure formed of glass or PDMS to increase light transmittance for polymer crosslinking. The inner-well mold structure had an outer diameter of 0.3 mm and 50 mm long while the outer wall mold structure had an inner diameter of 0.8 mm and the same length as in the inner wall mold. The inner wall mold structure was input into the outer wall mold structure to afford the mold with a space therebetween.

The reaction mixture was poured to the space between the inner and the outer wall mold structure and crosslinked in a UV crosslinker. In this regard, UV light (365 nm) was applied at an intensity of 290 mW/cm$^2$ to the polymer in the mold to manufacture a nasolacrimal duct insertion member.

Comparative Example 1. PCL (Poly(ε-Caprolactone)) Polymerization

Polymerization was conducted at the reactant ratio of [CL]$_0$/[HD]$_0$/[TBD]$_0$=100/0.5/1 as follows.

In a glass reactor (250 ml), CL (100 mmol, 9.97 ml) and HD (0.5 mmol, 60 mg) were mixed (see Table 6).

TABLE 6

|  | HD (mmol) | TBD (mmol) | HQ (mmol) | CL (mmol) | GMA (mmol) |
| --- | --- | --- | --- | --- | --- |
| Comparative Example 1 | 0.5 | 1 | — | 100 | — |

Then, when the inner temperature of the glass reactor having the two monomers mixed therein was judged to be thermally stable, TBD (1 mmol, 140 mg), as a catalyst for inducing the ring-opening polymerization of CL, was dissolved in 1 mL of acetonitrile and the solution was added to the glass reactor and stirred at 110° C. for 30 min. Subsequent procedures were performed in the same manner as in Example 1-1-1.

Comparative Example 2. PCL (Poly(ε-Caprolactone)) Polymerization-2

Polymerization was conducted at the reactant ratio of [CL]$_0$/[HD]$_0$/[TBD]$_0$=100/0.5/0.5 as follows.

In a glass reactor (250 ml), CL (100 mmol, 9.97 ml) and HD (0.5 mmol, 60 mg) were mixed (see Table 7).

TABLE 7

|  | HD (mmol) | TBD (mmol) | HQ (mmol) | CL (mmol) | GMA (mmol) |
| --- | --- | --- | --- | --- | --- |
| Comparative Example 2 | 0.5 | 0.5 | — | 100 | — |

Then, when the inner temperature of the glass reactor having the two monomers mixed therein was judged to be thermally stable, TBD (0.5 mmol, 70 mg), as a catalyst for inducing the ring-opening polymerization of CL, was dissolved in 1 mL of acetonitrile and the solution was added to the glass reactor and stirred at 110° C. for 1 hour. Subsequent procedures were performed in the same manner as in Example 1-1-1.

Experimental Example 1. Characterization of Shape Memory Polymer Prepared in Example 1

1-1. Preparation of Shape Memory Polymer Material Through UV Crosslinking

Figure 9:
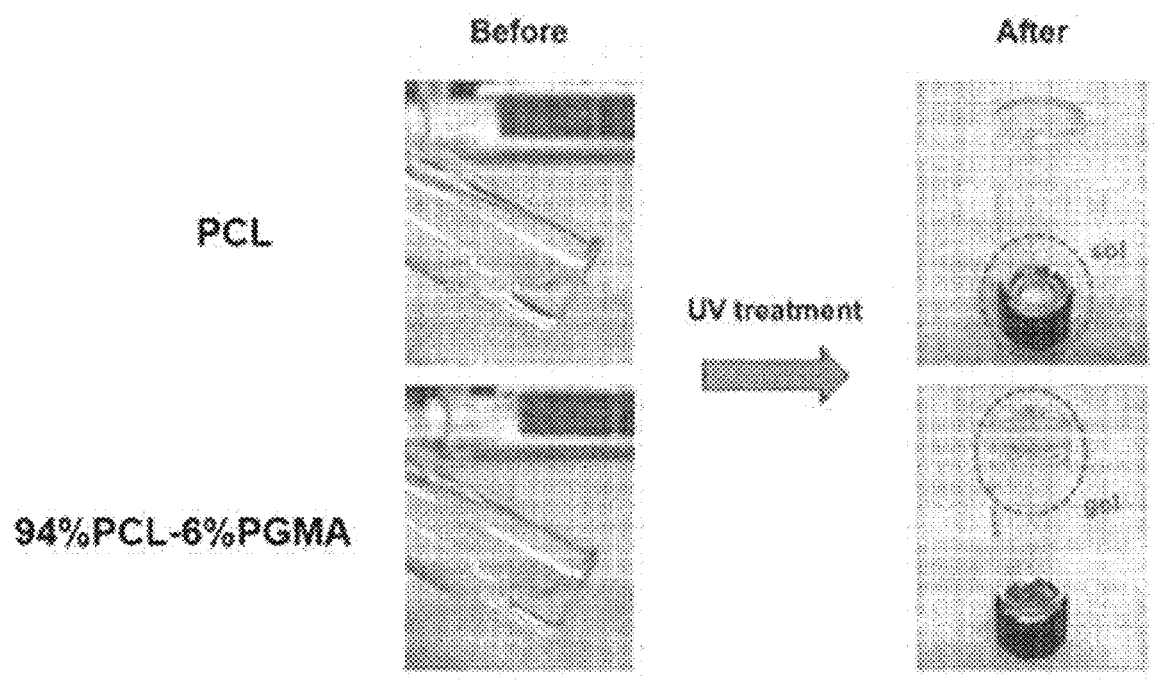
FIG. 9 is a view showing the comparison between phenomena observed after the polymers of Example 1-1 and Comparative Example 1 prepared in the present invention are treated with UV rays.

FIG. 9 is a view showing a comparison between phenomena observed after the polymers synthesized in Example 1-1-1 and Comparative Example 1 are treated with UV (ultraviolet) rays.

Referring to FIG. 9, the polymers synthesized in Example 1-1 and Comparative Example 1 were each mixed with a photoinitiator at a volume ratio of 10:1, and 400 μL of the resulting mixture was then put into a transparent glass container.

In brief, a 50 wt % dispersion of each of the polymers synthesized in Example 1-1-1 and Comparative Example 1 in dichloromethane was mixed at a volume ratio of 10:1 with a 10 wt % dispersion of a photoinitiator in dichloromethane.

Next, UV rays (320 to 500 nm) was applied to the glass container at an intensity of 14 W/cm$^2$ for 10 min.

Then, each of the UV-treated containers was turned upside down.

As a result, the polymer prepared in Example 1-1-1 was attached to the bottom surface of the glass container and were not easily detached therefrom, implying that UV treatment induced crosslinking between the modified acrylic groups to form a gel. On the other hand, the reaction mixture in Comparative Example 1 was in a liquid state and thus observed to remain unchanged in phase state.

That is, the polymer synthesized in Example 1-1 was cross-linkable by UV rays.

1-2. DSC Analysis-1

FIG. 10 and Table 8 show DSC analyses of the polymers of Example 1 and Comparative Example 1, respectively.

Briefly, physical properties of the polymer affected by the components and design variables were analyzed by differential scanning calorimetry (DSC) (T$_m$; melting temperature, βH$_m$; melting enthalpy, T$_c$; crystallization temperature, β$_{Hc}$; crystallization enthalpy).

TABLE 8

| Polymer | T$_m$(° C.) | ΔH$_m$(J/g) | T$_c$(° C.) | ΔH$_c$(J/g) |
| --- | --- | --- | --- | --- |
| Example 1 | 52.41 | 78.85 | 24.13 | 79.49 |
| Comparative Example 1 | 43.76 | 55.97 | 20.95 | 57.00 |

With reference to FIG. 10 and Table 8, the melting points were compared. As can be seen, the melting point of the PCL-co-PGMA synthesized in Example 1 was further low, compared to that of PCL in Comparative Example 1.

1-3. DSC Analysis-2

Figure 11:
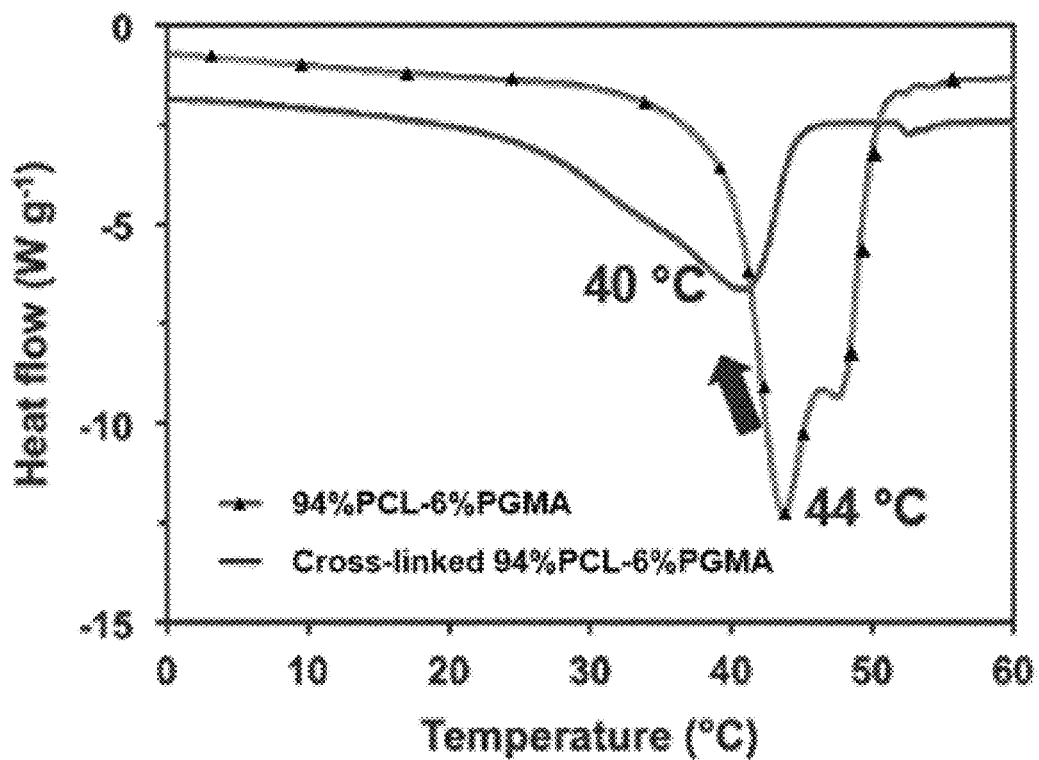
FIG. 11 shows DSC profiles of the polymers of Example 1-1 and Comparative Example 1 prepared in the present invention after UV treatment.

FIG. 11 and Table 9 show DSC analyses of the polymers of Example 1-1-1 and Comparative Example 1 after UV treatment, respectively.

TABLE 9

| Polymer | $XT_m$(° C.) | $\Delta H_m$(J/g) | $XT_c$(° C.) | $\Delta H_c$(J/g) |
|---|---|---|---|---|
| Comparative Example 1 | 52.05 | 67.17 | 23.17 | 65.17 |
| Example 1 | 40.44 | 43.01 | −1.73 | 26.32 |

Referring to FIG. 11 and Table 9, the melting point of the PCL-co-PGMA synthesized in Example 1 was observed to be further lowered, compared to that of PCL in Comparative Example 1. In particular, after UV treatment, the polymer synthesized in Example 1 had a melting point of 40.44° C., which was lower than when that of the polymer before UV treatment.

Experimental Example 2. Characterization of Examples 2-1 to 2-5 and Comparative Example 2

In Experimental Example 2, the polymers synthesized in Examples 2-1 to 2-4 and Comparative Example 2 were measured for melting point, and the UV-treated shape-memory polymers were subjected to DSC and GPC analyses.

The results are given in Table 12 and Table 11, below (FIG. 12(*a*): DSC analysis, FIG. 12(*b*): GPC analysis).

TABLE 10

| | x % PCL-y % PGMA | CL (mmol) | GMA (mmol) | HQ (mmol) | GMA (%) | $T_m$ (° C.) | $XT_m$ (° C.) |
|---|---|---|---|---|---|---|---|
| Comparative Example 2 | 100% PCL | 100 | — | — | — | 52.4 | 53.7 |
| Example 2-1 | 94% PCL-6% PGMA | 90 | 10 | 1 | 6.1 | 45.2 | 41.4 |
| Example 2-2 | 92% PCL-8% PGMA | 86 | 14 | 1.4 | 8.1 | 40.4 | 39.3 |
| Example 2-3 | 90% PCL-10% PGMA | 82 | 18 | 1.8 | 10.6 | 39.6 | 36.0 |
| Example 2-4 | 88% PCL-12% PGMA | 78 | 22 | 2.2 | 12.0 | 35.6 | 28.4 |

Figure 12:
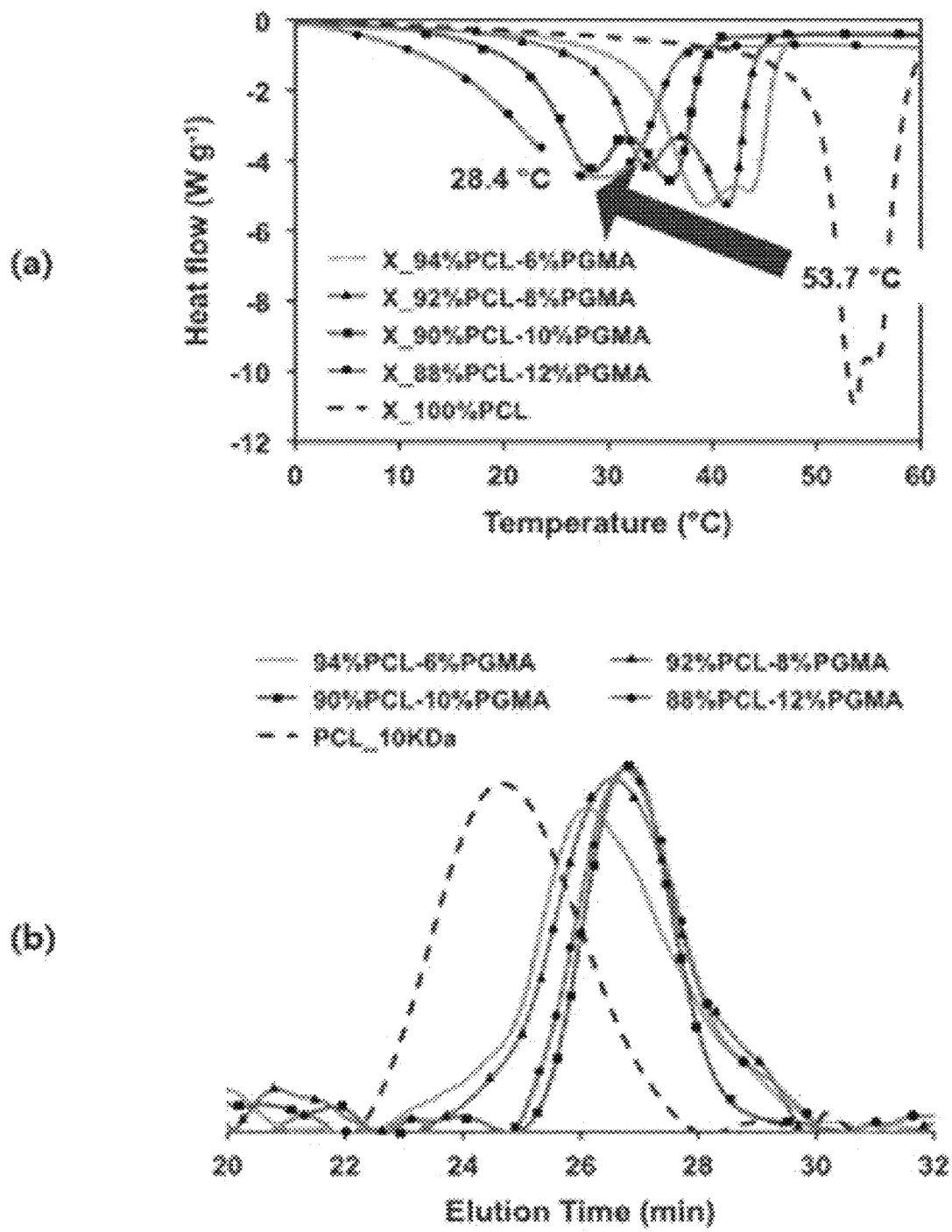
FIG. 12 shows characteristics of the polymers of Examples 2-1 to 2-4 and Comparative Example 2 prepared in the present invention ((a) DSC analysis, (b) GPC analysis).

Referring to FIG. 12 and Table 10, the characteristics of the polymers of Examples 2-1 to 2-4 and Comparative Example 2 were compared. As shown, the melting points of the PCL-co-PGMA shape-memory polymers synthesized in Examples 2-1 to 2-4 were further lowered, compared to that of the PCL synthesized in Comparative Example 2.

In particular, the melting point was lowered with the increasing of GMA contents. Also, the melting point ($XT_m$) of the polymer after UV treatment was lower than that ($T_m$) of the polymer before UV treatment.

In addition, referring to FIG. 12, the polymers were observed to have a molecular weight (Mw) less than the desired level 10 kDa, as measured by GPS analysis. Particularly, the molecular weight of the polymers was lowered with the increasing of GMA contents, indicating that the amorphous PGMA destroyed PCL crystallinity to lower the Tm and % crystallinity.

Experimental Example 3. Restoration of Shape Memory Polymer

Figure 13:
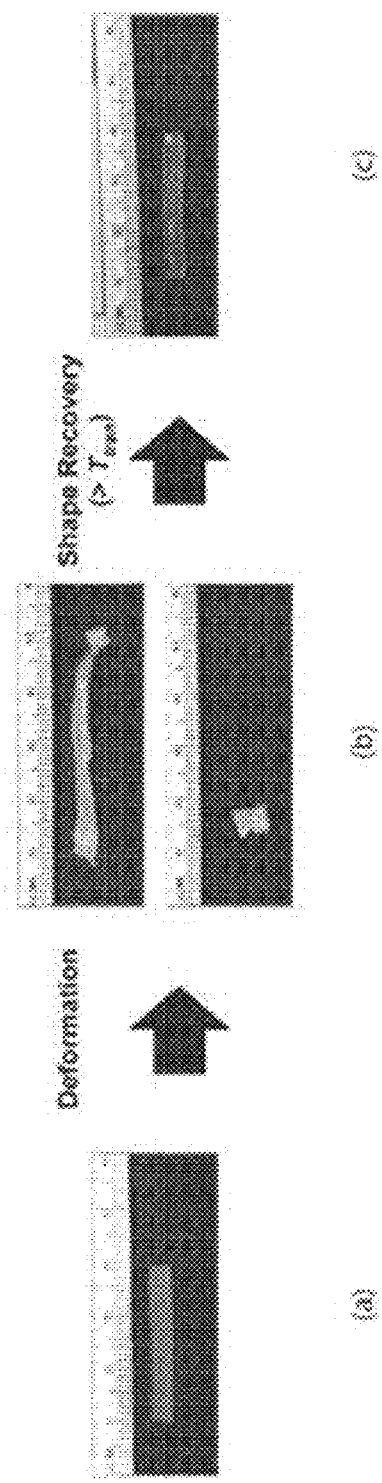
FIG. 13 shows photographic images of a shape memory polymer material that is deformed at a low temperature and then returns to an initial shape from the deformed temperature condition ((a) initial shape, (b) deformed shape at low temperature, and (c) restored shape).

The shape memory characteristics of the shape-memory polymer synthesized in Example 1 are shown in FIG. 13 ((A) initial state, (B) deformed state, and (C) restored state).

In brief, the shape-memory polymer material synthesized in Example 1 was deformed from the initial state when thermally treated at 60° C. (FIG. 13*b*). Also, the shape-memory polymer material returned to the initial state when the temperature was adjusted to the initial temperature of 35 to 40° C.

Next, the deformation recovery rate was measured.

The deformation recovery rate was determined, as follows: the polymer was prepared into a film which was then thermally treated at 60° C. and morphologically fixed for 3 min. Thereafter, the film was immersed in water at a temperature between 35 to 40° C. in consideration of the melting point of the polymer to measure a length of the polymer in a restored state (upper panel in FIG. 13*b*).

In another embodiment, the shape-memory polymer material synthesized in Example 1 was deformed from the initial state when thermally treated at −20° C. which is equal to or less than the crystallization temperature (lower panel in FIG. 13b)). Also, the shape-memory polymer material returned to the initial state when the temperature was adjusted to an initial temperature of 35 to 40° C.

Next, the deformation recovery rate was measured.

The deformation recovery rate is defined by Equation 1 below, and can be used as an indicator for shape memory behavior of a polymer resin.

$$\text{Deformation Recovery Rate } (Rr) = \{(l_e - l_r)/(l_e - l_o)\} \times 100 \quad [\text{Equation 1}]$$

wherein:

$l_o$: initial length of a sample;

$l_e$: length of a deformed sample; and $l_r$: length of the sample after recovery.

Therefore, the 90% PCL-co-10% PGMA shape-memory polymer material treated with UV rays in Example 4 was measured to have as a deformation recovery rate of 90% or greater, which accounts for the excellent resilience of the shape-memory polymer material. In addition, the shape-memory polymer material had a low melting point and thus is considered to be suitable as a biomaterial.

Experimental Example 4. Properties of Shape Memory Polymer 4-1. Measurement of Compressive Strength of Shape Memory Polymer The polymer 94% PCL-co-6% PGMA synthesized in Example 1-1 was measured for strength, structure, and melting point.

Specifically, measurement was made using the following methods.

Young's modulus

Measurement was made using a test method according to ASTM D412.

Polymer structure

Components in the synthesized polymer (the ratio of PCL and PGMA repeat units in terms of the ratio of hydrogen atoms in PCL and PGMA) were measured using $^1$H NMR (nuclear magnetic resonance).

Melting point (° C.)

The melting point of the polymer was analyzed by DSC (differential scanning calorimetry).

TABLE 11

|  | Young's modulus (MPa) | Degree of crosslinking (%) | Melting point (° C.) |
|---|---|---|---|
| Example 1-1-1 | 50 w/v % | 0.039 | 66.9 | 36.31 |
| Example 1-1-2 | 75 w/v % | 0.178 | 85.4 | 32.96 |
| Example 1-1-3 | 100 w/v % | 0.317 | 90.9 | 30.92 |

As a result, the strength, the degree of crosslinking, and the melting point were observed to vary depending on the mass of the shape memory polymer dissolved based on the solvent. That is, when the mass % of the shape memory polymer dissolved in the solvent was adjusted, the Young's modulus representing the strength was changed, and accordingly, the degree of crosslinking and melting point (shape restoration temperature) were also controllable 4-2. Measurement of Contact Angle of Shape Memory Polymer One drop (10 μg) of distilled water was placed on the surface of each of the polymer (PCL) of Comparative Example 1 and the shape memory polymers (96% PCL-co-4% PGMA polymer, 94% PCL-co-6% PGMA polymer, and 92% PCL-co-8% PGMA polymer) and photographed to analyze contact angles. The results are given in FIG. 14.

In addition, the polymer of Comparative Example 1 and the shape memory polymers were crosslinked by UV rays in the same manner as in Example 2 and analyzed for contact angle as described above.

Figure 14:
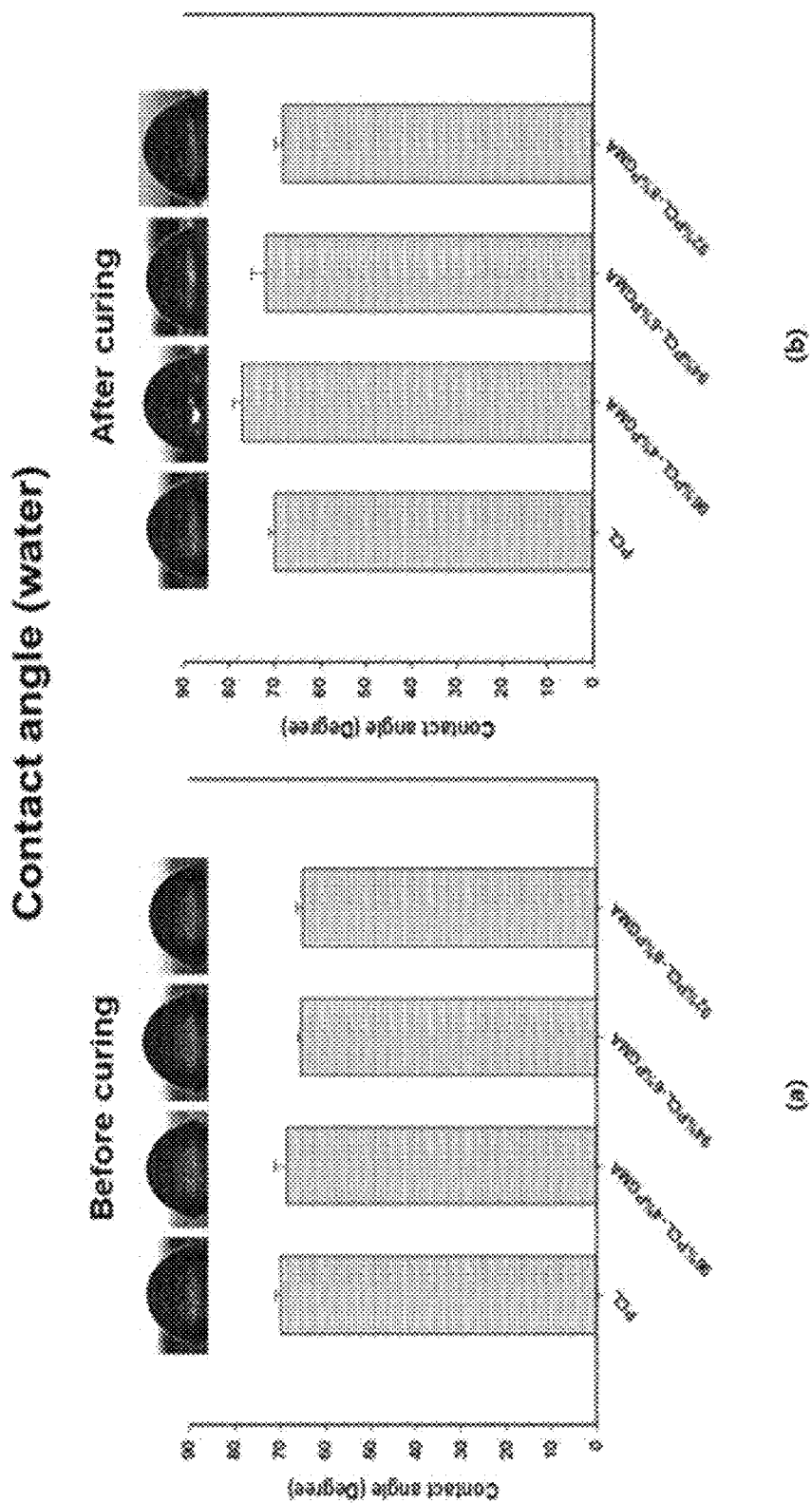
FIG. 14 is a view showing contact angles of shape memory polymers of the present invention ((a) pre-crosslinking, and (b) post-crosslinking).

Referring to FIG. 14, the shape memory polymers with different compositions, whether crosslinked or not, were not significantly different in hydrophobicity from PCT, which is representative of polymers commonly used as biodegradable insertion members.

Experimental Example 5. Cytotoxicity

The nasolacrimal duct insertion member (94% PCL-co-6% PGMA) prepared in Example 3 was analyzed for cytotoxicity. To this end, L929 cells (mouse cell line) were cultured in a control (cell/tissue culture plate) and on a polymer film of the nasolacrimal duct insertion member.

Figure 15:
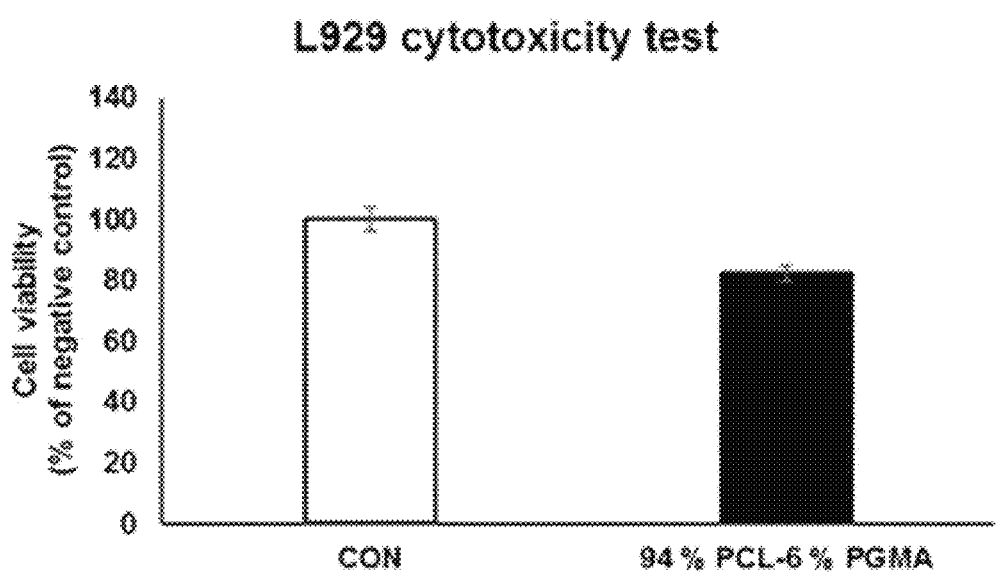
FIG. 15 is a graph showing cell viability after L929 cells have been cultured in a control environment and on a film of the shape memory polymer (94% PCL-co-6% PGMA) synthesized in Example 1.

Then, cell viability was measured, and the results are depicted in FIG. 15. FIG. 15 is a graph showing cell viability after L929 cells have been cultured in a control environment and on a film of the shape memory polymer (94% PCL-co-6% PGMA) synthesized in Example 1.

Referring to FIG. 15, the polymer of the present invention guarantees a cell viability of 80% or more, which is sufficient for the approval of the FDA.

Experimental Example 6. Measurement of Cell Proliferation Rate

The nasolacrimal duct insertion member manufactured in Example 3 was analyzed for cell attachment and proliferation rates.

Figure 16:
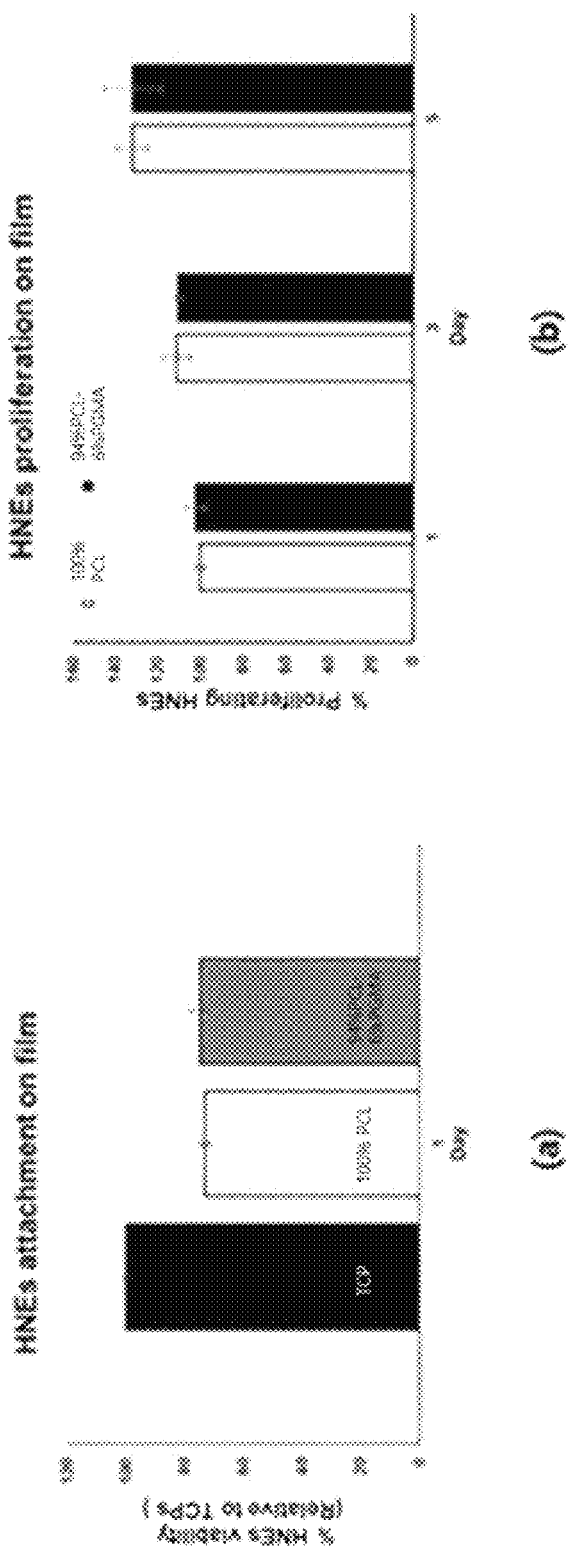
FIG. 16 shows attachment % and proliferation % of NHEs on TCPS, PCL, and 94% PCL-co-6% PGMA ((a) % attachment of HNEs, (b) % proliferation of HNEs).

In brief, human nasal epithelial cells (HNEs) which come in contact with the member inserted into the nasolacrimal duct were cultured and measured for attachment rate and proliferation rate after attachment. The results are depicted in FIG. 16. FIG. 16 shows attachment % and proliferation % of NHEs on TCPS, PCL, and 94% PCL-co-6% PGMA ((a) % attachment of HNEs, (b) % proliferation of HNEs).

With reference to FIG. 16, an incubator (tissue culture plate: TCPS) and 100% PCL (polycaprolactone) were employed as comparison groups, and HNEs were observed to attach to each of PCL and 94% PCL-co-6% PGMA at about 70% or higher, relative to 100% for TCPS.

In addition, proliferation was measured in the comparative groups. Relative to 100% for TCPS, the proliferation rates were detected near 100% for both PCL and 94% PCL-co-6% PGMA from day 1 and was remarkably increased to about 140% on day 5.

Consequently, the data indicate that the nasolacrimal duct insertion member of Example 3 has no influences on the attachment and proliferation of human nasal epithelial cells which comes in contact with the member when it is inserted into the nasolacrimal duct.

Experimental Example 7. Recovery of Nasolacrimal Duct Insertion Member

Figure 17:
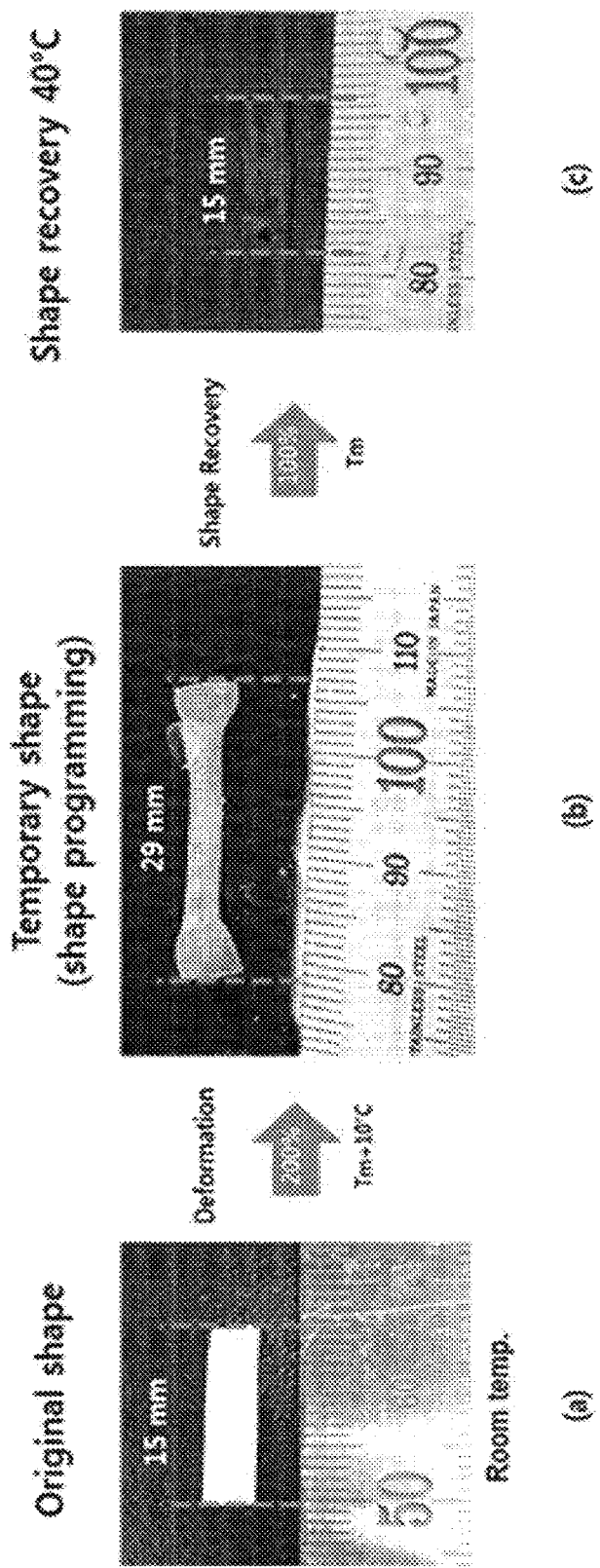
FIG. 17 is a view showing a process in which the nasolacrimal duct insertion member manufactured prepared in Example 3 returns to an initial state from a deformation temperature condition ((a) initial shape, (b) deformed shape, (c) recovered shape (40° C.)).

FIG. 17 is a view showing a process in which the nasolacrimal duct insertion member manufactured prepared in Example 3 returns to an initial state from a deformation temperature condition ((a) initial state, (b) deformed state, (c) recovered state (40° C.)). That is, FIG. 17 is a view demonstrating the feasibility of the nasolacrimal duct insertion member.

Referring to FIG. 17, a thick tube insert 15 mm long is elongated to 29 mm in length with the diameter decreasing, in a temporary state (temporary shape) before insertion into the nasolacrimal duct. After being insert into the nasolacrimal duct, when the temperature was elevated to 40° C., the insert was reduced to 15 mm in length with the diameter increasing. In other words, the possibility of shape memory programming was confirmed.

Figure 18:
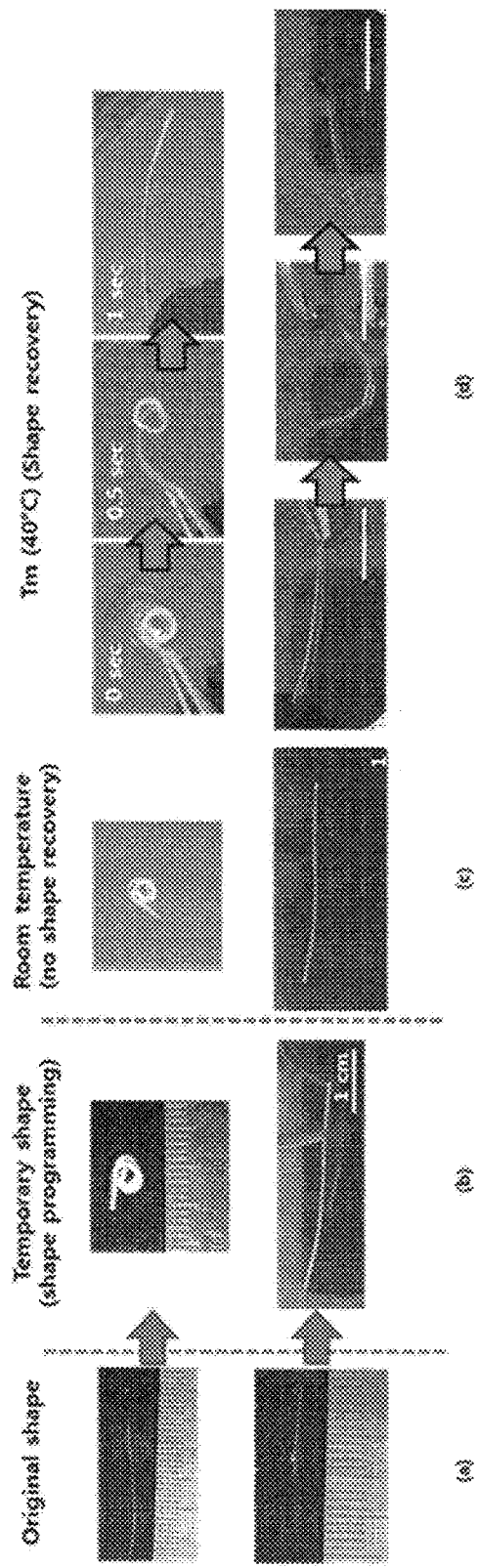
FIG. 18 is a view showing a process in which the nasolacrimal duct insertion member manufactured prepared in Example 3 returns to an initial state under a deformation temperature condition ((a) initial shape, (b) deformed shape, (c) deformed shape (room temperature), and (d) recovered state (40° C.)).

FIG. 18 is a view showing a process in which the nasolacrimal duct insertion member manufactured prepared in Example 3 returns to an initial state under a deformation temperature condition ((a) initial state, (b) deformed state, (c) deformed state (room temperature), and (d) recovered state (40° C.)).

Referring to FIGS. 18(a) and (b), it is possible to conduct the shape programming from an initial shape (post-insertion shape: a tube shape with the inside blocked) to a temporary shape (coil shape or elongated shape).

The shape-programmed insert could not restore the initial shape at room temperature (FIG. 18 (c)), but returned to the initial shape when the temperature was increased to 40° C. after insertion.

As a consequence, the data of Experimental Example 7 demonstrate that the shape-memory polymer material has excellent deformation recovery rate and extraordinary ability to recover any shape and is suitable as a biomaterial due to its low melting point.

Experimental Example 8. Observation of Tissue Reaction of Lacrimal Duct Insertion Member after Application Tissue reactions were observed 2 weeks after inserting the nasolacrimal duct insertion member manufactured in Example 3 and a nasolacrimal duct insertion member made of silicone into the nasal ducts of normal rabbits.

Figure 19:
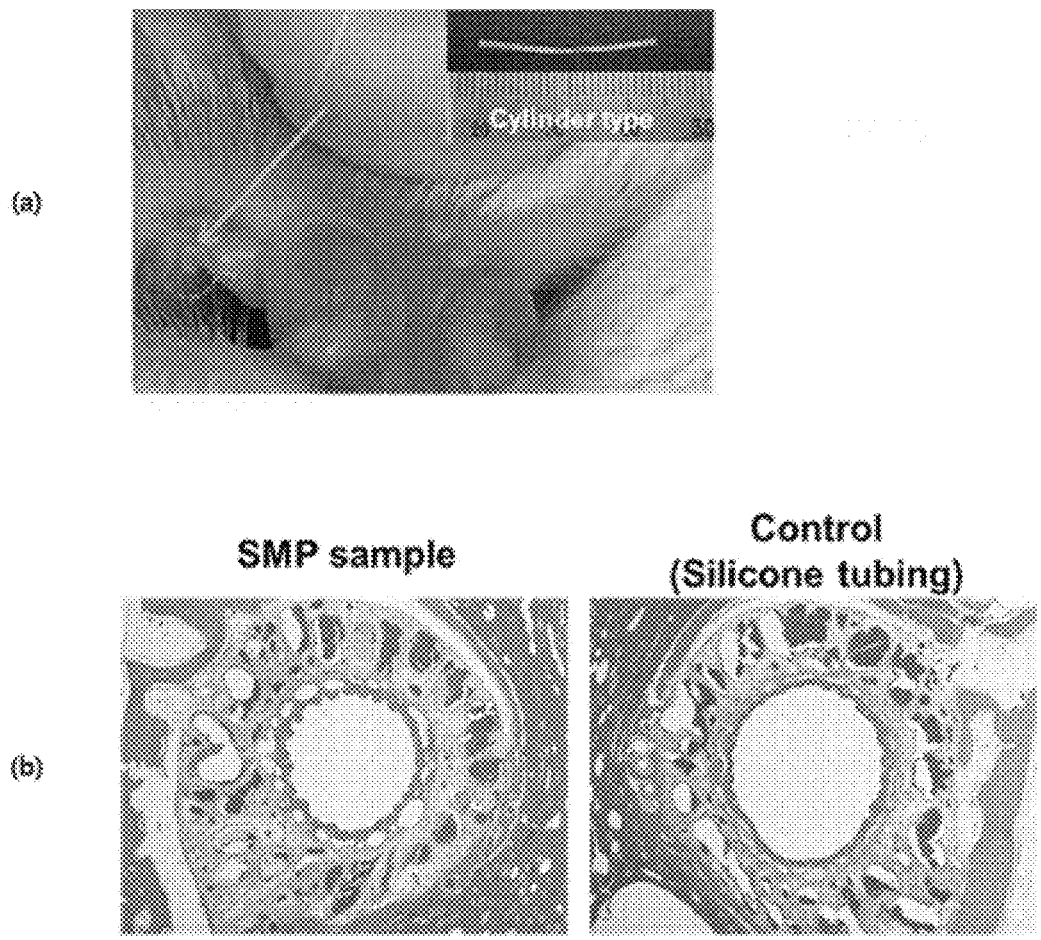
FIG. 19 shows photographic images illustrating the nasolacrimal duct of a normal rabbit into which the nasolacrimal duct insertion member manufactured in Example 3 and a nasolacrimal duct insertion member made of silicone were inserted (a); and tissue reactions 2 weeks after insertion of the nasolacrimal duct insertion members (b) (left: the nasolacrimal duct insertion member of the present invention, and right: silicone).

FIG. 19 shows photographic images illustrating the nasolacrimal duct of a normal rabbit into which the nasolacrimal duct insertion member manufactured in Example 3 and a nasolacrimal duct insertion member made of silicone were inserted (a); and tissue reactions 2 weeks after insertion of the nasolacrimal duct insertion members (b) (left: the nasolacrimal duct insertion member of the present invention, and right: silicone).

As can be seen, the nasolacrimal duct insertion member manufactured in Example 3 did not induce an inflammatory reaction or tissue abnormality, like the silicone tube.

DESCRIPTION OF REFERENCE NUMERALS

1, 1': lacrimal punctum

2: lacrimal sac

3: nasolacrimal duct

10: nasolacrimal duct insertion member

INDUSTRIAL APPLICABILITY

The present invention relates to a nasolacrimal duct insertion member comprising a shape memory polymer for treatment of nasolacrimal duct obstruction/stenosis. Based on a shape memory polymer bearing a crosslinkable functional group, the nasolacrimal duct insertion member can be provided with a melting point suitable for bio-implantation.

What is claimed is:

1. A tubular device for expanding nasolacrimal duct,
wherein the device has a restored cross-sectional thickness of 50 to 200 μm, a restored inner diameter of 0.4 to 1.2 mm, and a restored length of 10 to 50 mm within the nasolacrimal duct upon exposure to physiological temperature of 28 to 42° C., and
wherein the device comprises a shape memory polymer represented by the following Chemical Formula 1:

[Chemical Formula 1]

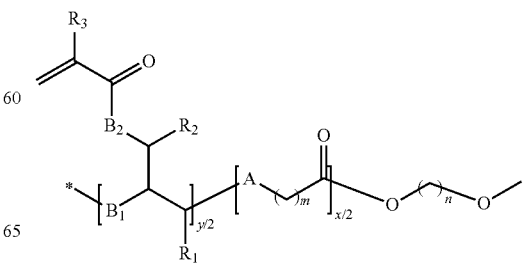

-continued

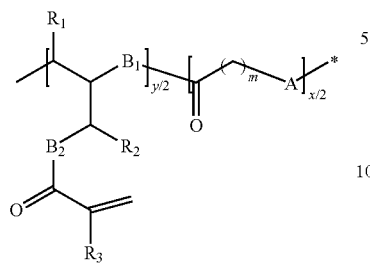

wherein, $R_1$, $R_2$, and $R_3$ are each independently hydrogen (H) or an alkyl of 1 to 6 carbon atoms, m and n are each an integer of 1 to 20, A, $B_1$, and $B_2$ are each independently oxygen (O) or sulfur(S), x and y represent mole % for respective repeat units, and x+y is 100, and x is 80 to 95.

2. The tubular device of claim 1, wherein, $R_1$, $R_2$, and $R_3$ are each independently hydrogen (H) or a methyl group, m and n are each an integer of 3 to 12, A, $B_1$, and $B_2$ are each independently oxygen (O) or sulfur(S), x and y represent mole % for respective repeat units, and x+y is 100, and x is 88 to 94.

3. The tubular device of claim 1, wherein the shape memory polymer has an average melting temperature of 30 to 48° C.

4. The tubular device of claim 1, wherein the shape memory polymer has an average melting point of 28 to 42° C. after being crosslinked.

5. The tubular device of claim 1, comprising a shape memory polymer represented by the following Chemical Formula 2:

[Chemical Formula 2]

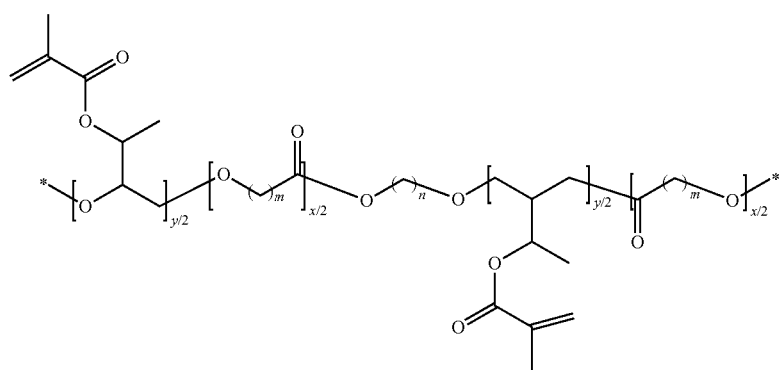

wherein,
m and n are each an integer of 1 to 20,
x and y represent mole % for respective repeat units, and
x+y is 100, and x is 80 to 95.

* * * * *